(12) United States Patent
Bertrand et al.

(10) Patent No.: US 12,030,840 B2
(45) Date of Patent: Jul. 9, 2024

(54) ELAFIBRANOR SALTS

(71) Applicant: GENFIT, Loos (FR)

(72) Inventors: Karine Bertrand, Frelinghien (FR);
Alice Roudot, Lomme (FR);
Marie-Jeanne Joissains, Plomelin (FR)

(73) Assignee: GENFIT, Loos (FR)

( * ) Notice: Subject to any disclaimer, the term of this patent is extended or adjusted under 35 U.S.C. 154(b) by 703 days.

(21) Appl. No.: 17/265,058

(22) PCT Filed: Aug. 2, 2019

(86) PCT No.: PCT/EP2019/070877
§ 371 (c)(1),
(2) Date: Feb. 1, 2021

(87) PCT Pub. No.: WO2020/025789
PCT Pub. Date: Feb. 6, 2020

(65) Prior Publication Data
US 2021/0309608 A1 Oct. 7, 2021

(30) Foreign Application Priority Data

Aug. 3, 2018 (EP) .................................... 18306060

(51) Int. Cl.
*C07C 323/62* (2006.01)
*A61P 1/16* (2006.01)
*C07C 319/28* (2006.01)
(52) U.S. Cl.
CPC .............. *C07C 323/62* (2013.01); *A61P 1/16* (2018.01); *C07C 319/28* (2013.01); *C07B 2200/13* (2013.01)

(58) Field of Classification Search
CPC ... C07C 323/62; C07C 211/27; C07C 215/08; C07C 215/10; C07C 215/40; C07C 229/04; C07C 229/08; A61P 1/16; C07B 2200/13; C07D 207/06
See application file for complete search history.

(56) References Cited

FOREIGN PATENT DOCUMENTS

WO 2018/060372 4/2018
WO WO-2018060372 A1 * 4/2018 ........... A61K 31/192

OTHER PUBLICATIONS

Stephen Byrn, et al., "Pharmaceutical Solids: A Strategic Approach to Regulatory Considerations", Pharmaceutical Research, vol. 12, No. 7, 1995, pp. 945-954 (10 pages).
Laurence M. Harwood, et al., "Experimental Organic Chemistry—Principles and Practice", Blackwell Science, 1989, pp. 127-132 (8 pages).
"Chapter 11, Tools for Purifying the Product: Column Chromatography Crystallization and Reslurrying", In: Anderson: "Practical Process Research & Development", Academic Press, 2000, pp. 223-224 (2 pages).
International Search Report and Written Opinion of the ISA for PCT/EP2019/070877 dated Nov. 21, 2019, 18 pages.

* cited by examiner

*Primary Examiner* — Deborah D Carr
(74) *Attorney, Agent, or Firm* — NIXON & VANDERHYE, PC

(57) ABSTRACT

The present invention relates to salts of elafibranor.

8 Claims, 14 Drawing Sheets
Specification includes a Sequence Listing.

FIGURE 4a
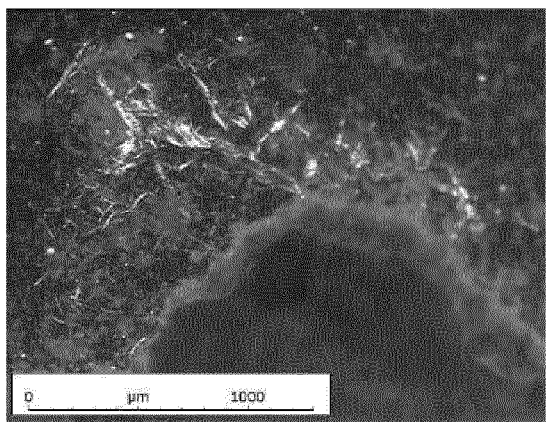 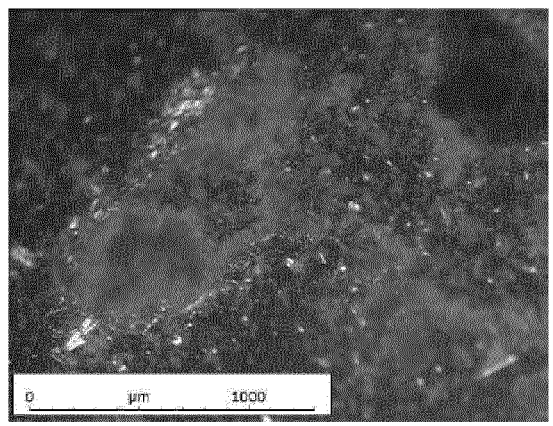
FIGURE 4b
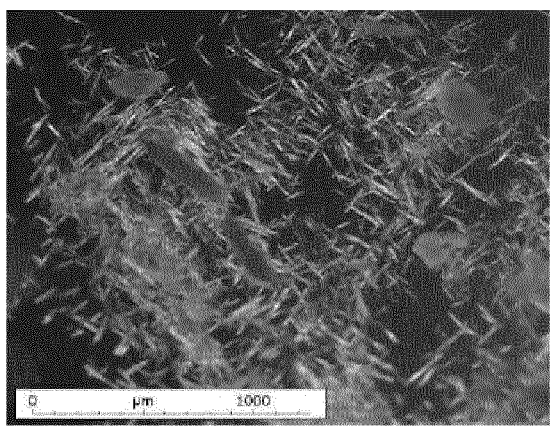 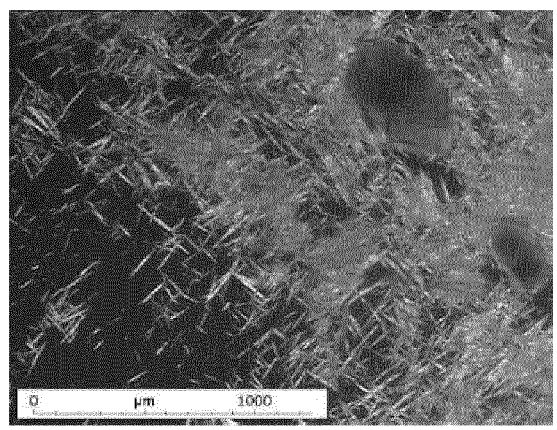
FIGURE 5
FIGURE 6
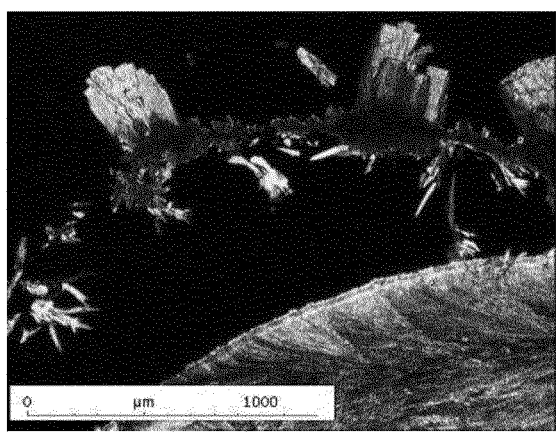 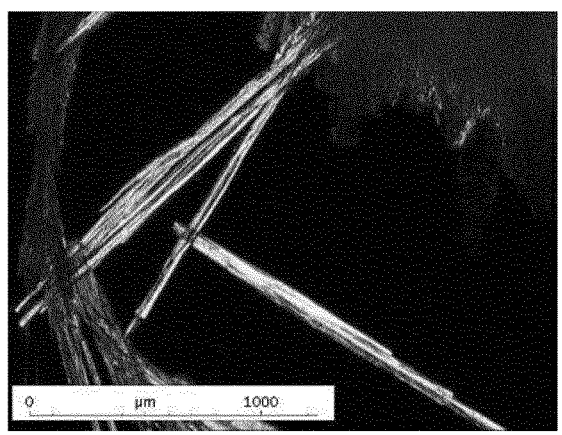

Elafibranor

Elafibranor sodium salt

Elafibranor L-arginine salt

Elafibranor potassium salt

Elafibranor tromethamine salt

Elafibranor

Elafibranor sodium salt

Elafibranor L-arginine salt

Elafibranor potassium salt

Elafibranor tromethamine salt

SEQUENCE LISTING

<160> NUMBER OF SEQ ID NOS: 8

<210> SEQ ID NO 1
<211> LENGTH: 25
<212> TYPE: DNA
<213> ORGANISM: artificial
<220> FEATURE:
<223> OTHER INFORMATION: primer

<400> SEQUENCE: 1
catgctcaac atctccccct tctcc                                                25

<210> SEQ ID NO 2
<211> LENGTH: 25
<212> TYPE: DNA
<213> ORGANISM: artificial
<220> FEATURE:
<223> OTHER INFORMATION: primer

<400> SEQUENCE: 2
gggaaggtgt aatccgtctc cacag                                                25

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
aatggtgctc ctggtattgc                                                      20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
accaggttca ccgctgttac                                                      20

<210> SEQ ID NO 5
<211> LENGTH: 25
<212> TYPE: DNA
<213> ORGANISM: artificial
<220> FEATURE:
<223> OTHER INFORMATION: primer

<400> SEQUENCE: 5
catgctcaac atctccccct tctcc                                                25

<210> SEQ ID NO 6
<211> LENGTH: 25
<212> TYPE: DNA
<213> ORGANISM: artificial
<220> FEATURE:
<223> OTHER INFORMATION: primer

<400> SEQUENCE: 6
catgctcaac atctccccct tctcc                                                25

<210> SEQ ID NO 7
<211> LENGTH: 20
<212> TYPE: DNA
<213> ORGANISM: artificial

```
<220> FEATURE:
<223> OTHER INFORMATION: primer

<400> SEQUENCE: 7
gttggtctac cgggactcaa                                           20

<210> SEQ ID NO 8
<211> LENGTH: 20
<212> TYPE: DNA
<213> ORGANISM: artificial
<220> FEATURE:
<223> OTHER INFORMATION: primer

<400> SEQUENCE: 8
gttcacctct gatcccctga                                           20
```

ELAFIBRANOR SALTS

This application is the U.S. national phase of International Application No. PCT/EP2019/070877 filed Aug. 2, 2019 which designated the U.S. and claims priority to EP Patent Application No. 18306060.7 filed Aug. 3, 2018, the entire contents of each of which are hereby incorporated by reference.

TECHNICAL FIELD

The present invention relates to salts of elafibranor, methods for their preparation and uses thereof.

BACKGROUND

Elafibranor, of Formula (I)

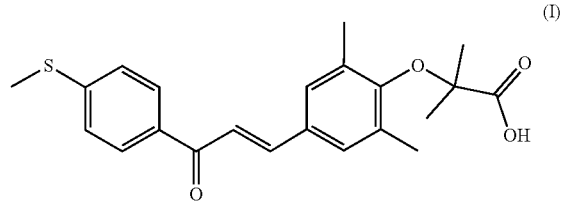 [SMILES: CSc1ccc(C(=O)/C=C/c2cc(C)c(OC(C)(C)C(=O)O)c(C)c2)cc1]

is a molecule currently evaluated in a phase III clinical study for the treatment of non-alcoholic steatohepatitis (NASH). Elafibranor, its manufacture and uses are described in WO2004005233 and WO2011144579.

Studies conducted by the inventors have shown that physicochemical properties of elafibranor, such as its stability (in particular its photostability) and solubility, may be improved.

It has now been found that the physicochemical properties of elafibranor can be further improved by converting the free acid of elafibranor into a salt of elafibranor.

SUMMARY OF INVENTION

The invention relates to salts of elafibranor and methods for preparing the same.

The present invention also provides a pharmaceutical composition comprising a therapeutically effective amount of a salt of the invention and a pharmaceutically acceptable carrier.

The invention further provides a combination comprising a salt of the invention and one or more other therapeutic agents.

The invention also provides a salt of the invention for use in therapy. In particular, the salt of the invention may be used for the treatment of liver diseases in particular NAFLD (non-alcoholic fatty liver disease), NASH (non-alcoholic steatohepatitis), liver fibrosis, or cirrhosis. The invention further provides use of a salt of the invention in the manufacture of a medicament, such as a medicament for the treatment of a liver disease, in particular NAFLD (non-alcoholic fatty liver disease), NASH (non-alcoholic steatohepatitis), liver fibrosis, or cirrhosis.

The invention also provides a method for treating a subject afflicted with liver disease in particular NAFLD (non-alcoholic fatty liver disease), NASH (non-alcoholic steatohepatitis), liver fibrosis or cirrhosis, comprising administering to said subject therapeutically effective amount of a salt of the invention.

In a particular embodiment, the invention may be used for the treatment of NAFLD (non-alcoholic fatty liver disease), NASH (non-alcoholic steatohepatitis) or cirrhosis.

DESCRIPTION OF THE FIGURES AND TABLES

Figure 1:
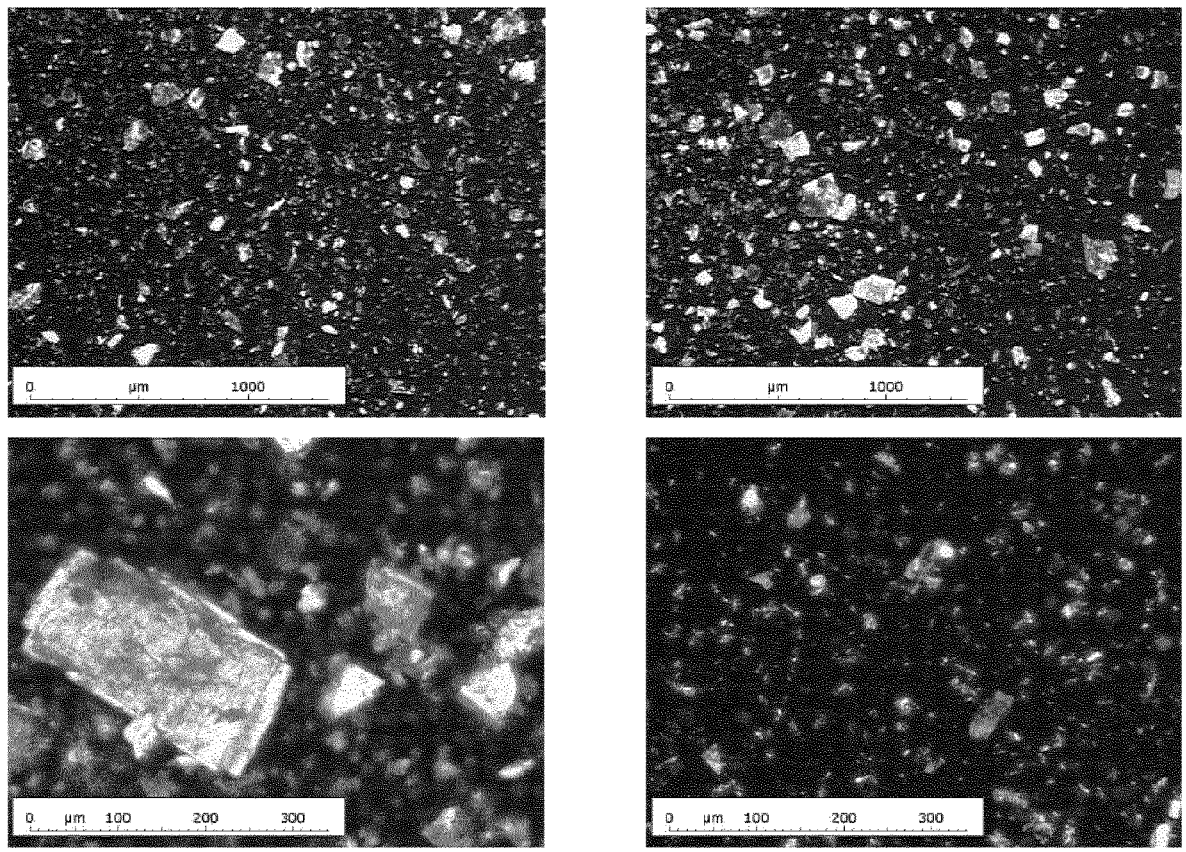

Abbreviations used in the figures, in the tables, and in the text:
AcOEt Ethyl acetate
CH3CN Acetonitrile
c.p.s. count per second
DSC Differential Scanning calorimeter
EtOH Ethanol
$H_2O$ Water
IPA Isopropyl alcohol
Potassium chloride KCl
$Na_2HPO_4$ Di-sodium hydrogenophosphate
NAFLD non-alcoholic fatty liver disease
NaOH Sodium hydroxide
NASH non-alcoholic steatohepatitis
OM Optical Microscopy
RH relative humidity
THF Tetrahydrofuran
XRPD X-ray powder diffraction FIG. 1: Optical Microscopy of Salt I
FIG. 1 shows optical microscopy for Salt I crystallized in EtOH/AcEt under cross-polarized light (magnification up ×81 and down ×325)

Figure 2A:
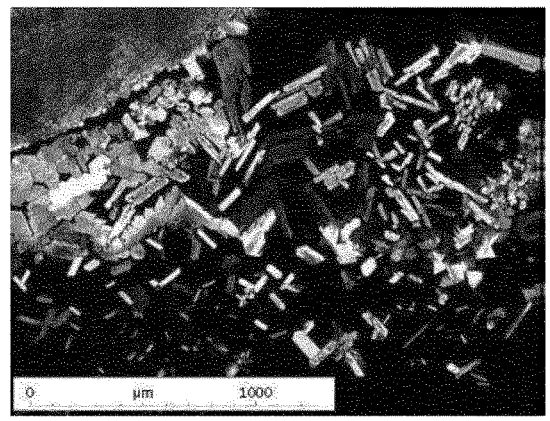
Figure 2B:
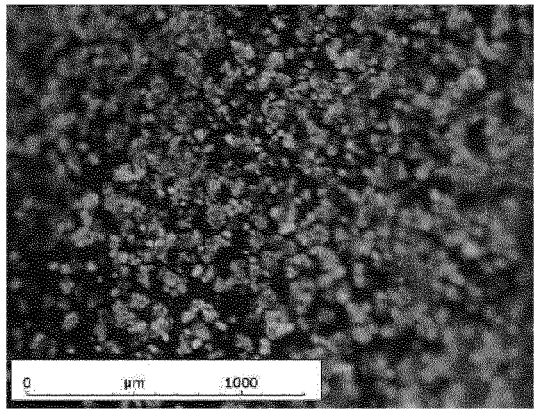
Figure 2B:
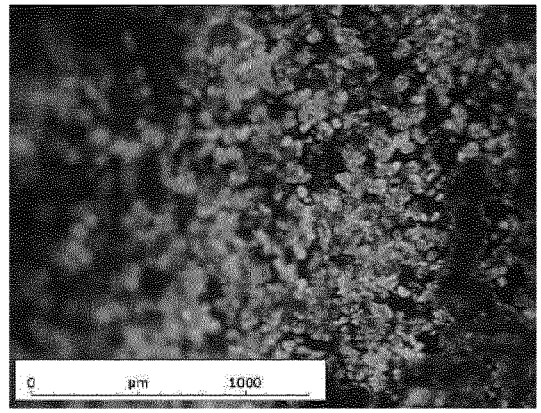
Figure 2C:
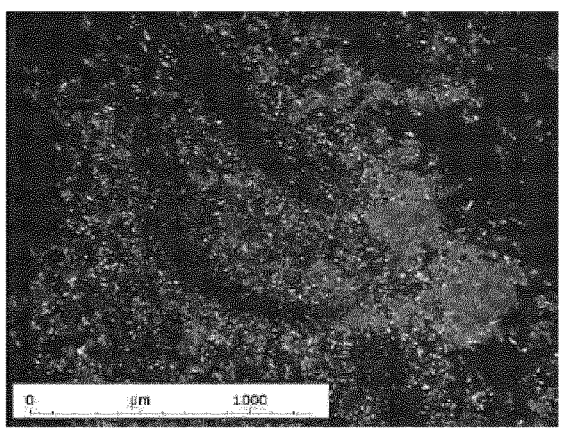
Figure 2C:
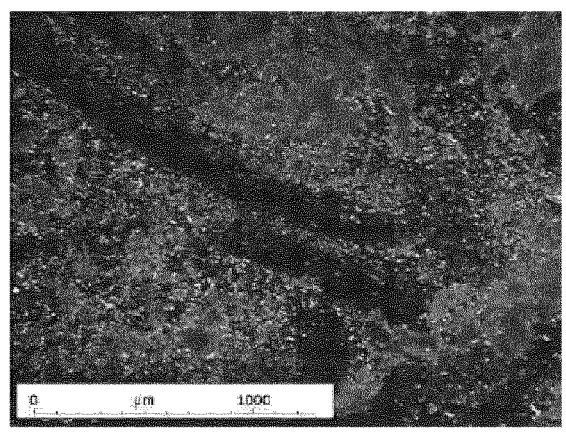

FIGS. 2a, 2b and 2c: Optical Microscopy of Salt II
FIG. 2a shows optical microscopy for Salt II re-crystallized in IPA under cross-polarized light (Magnification ×84).
FIG. 2b shows optical microscopy for Salt II re-crystallized in IPA/$H_2O$ under cross-polarized light (Magnification ×81).
FIG. 2c shows optical microscopy for Salt II re-crystallized in CH3CN under cross-polarized light (Magnification ×81).

Figure 3:
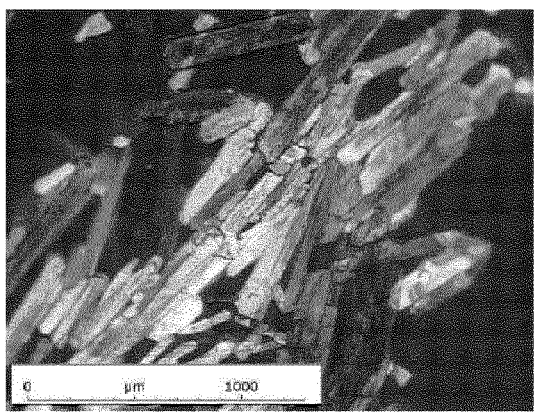
Figure 3:
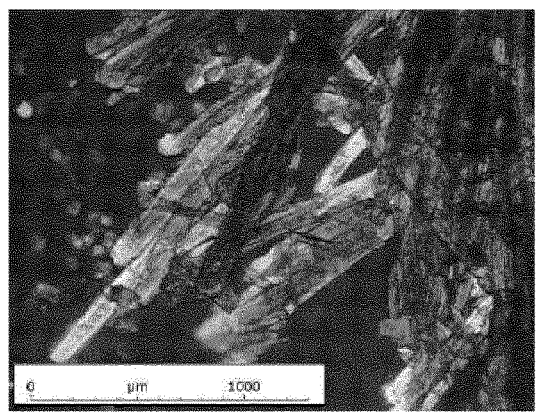

FIG. 3: Optical Microscopy of Salt III
FIG. 3 shows optical microscopy for Salt III crystallized in acetone under cross-polarized light (Magnification ×81).

FIGS. 4a, and 4b: Optical Microscopy of Salt IV
FIG. 4a shows optical microscopy for Salt IV re-crystallized in acetone under cross-polarized light (Magnification ×81).
FIG. 4b shows optical microscopy for Salt IV re-crystallized in acetone/$H_2O$ under cross-polarized light (Magnification ×81).

FIG. 5: Optical Microscopy of Salt V
FIG. 5 shows optical microscopy for Salt V re-crystallized in acetone/$H_2O$ under cross-polarized light (Magnification ×84).

FIG. 6: Optical Microscopy of Salt VI
FIG. 6 shows optical microscopy for Salt VI re-crystallized in acetone/$H_2O$ under cross-polarized light (Magnification ×25).

Figure 7:
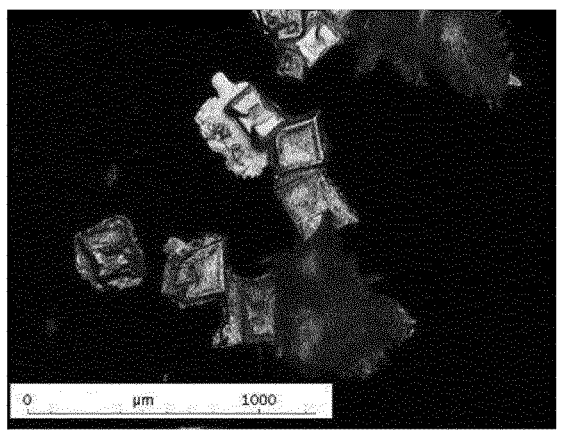

FIG. 7: Optical Microscopy of Salt VII
FIG. 7 shows optical microscopy for Salt VII re-crystallized in acetone/$H_2O$ under cross-polarized light (Magnification ×84).

Figure 8:
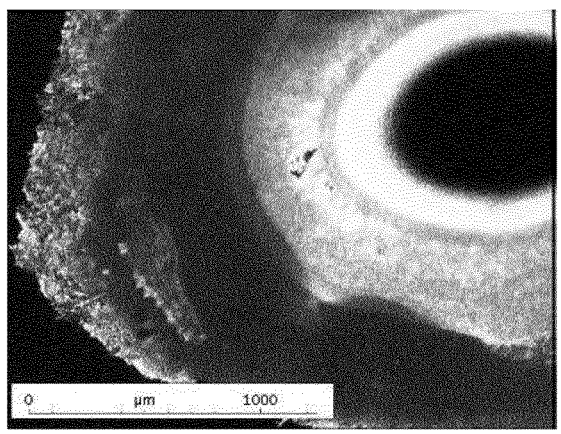

FIG. 8: Optical Microscopy of Salt VIII
FIG. 8 shows optical microscopy for Salt VIII re-crystallized in acetone under cross-polarized light (Magnification ×84).

Figure 9:
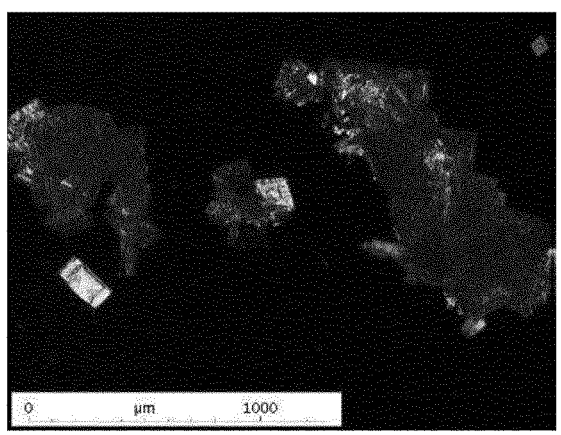

FIG. 9: Optical Microscopy of Salt IX
FIG. 9 shows optical microscopy for Salt IX re-crystallized in acetone/$H_2O$ under cross-polarized light (Magnification ×84).

Figure 10:
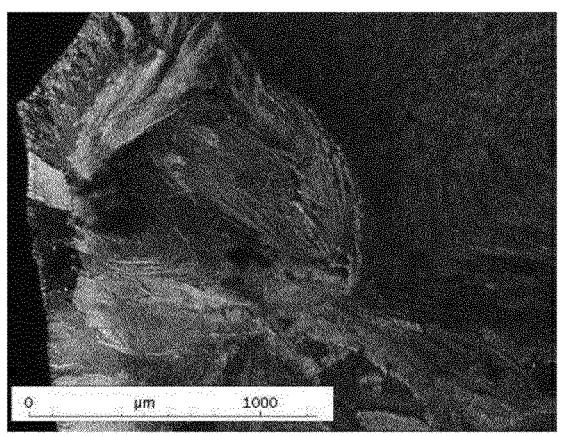
Figure 11:
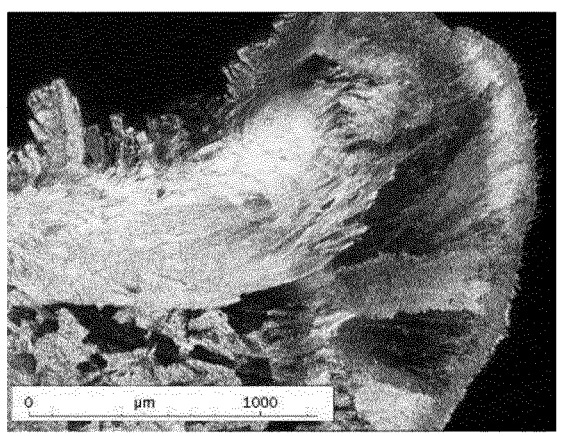
Figure 12:
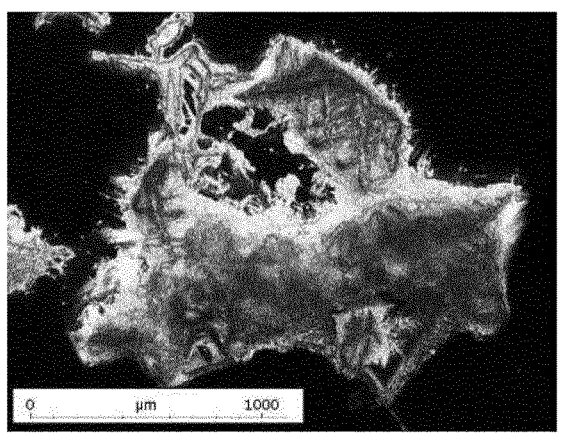
Figure 13:
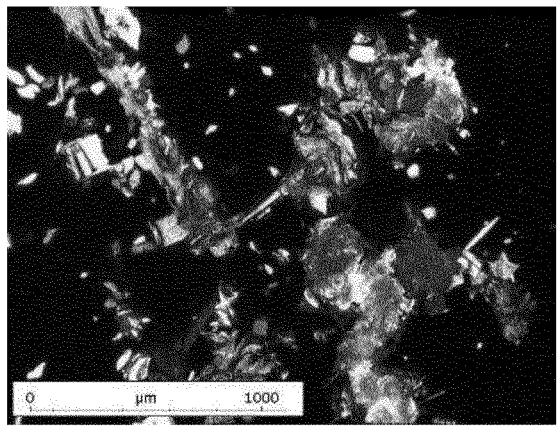
Figure 14:
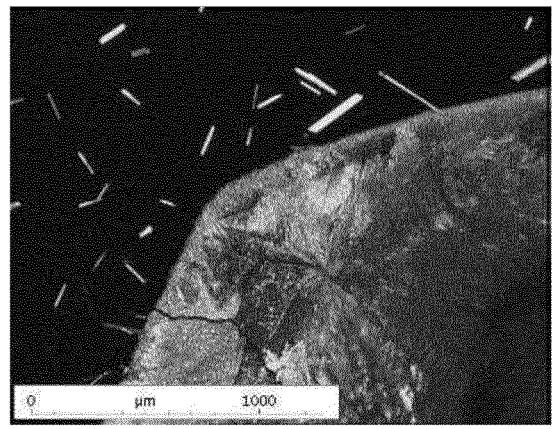
Figure 15:
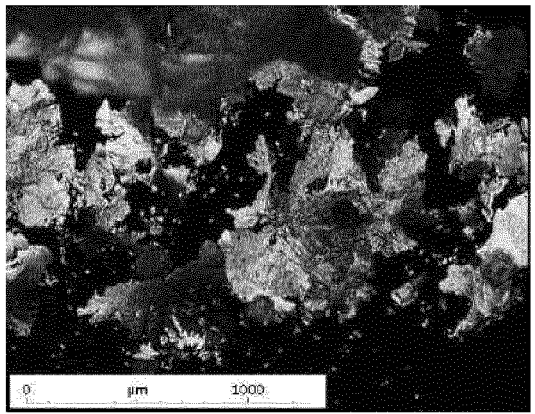
Figure 16:
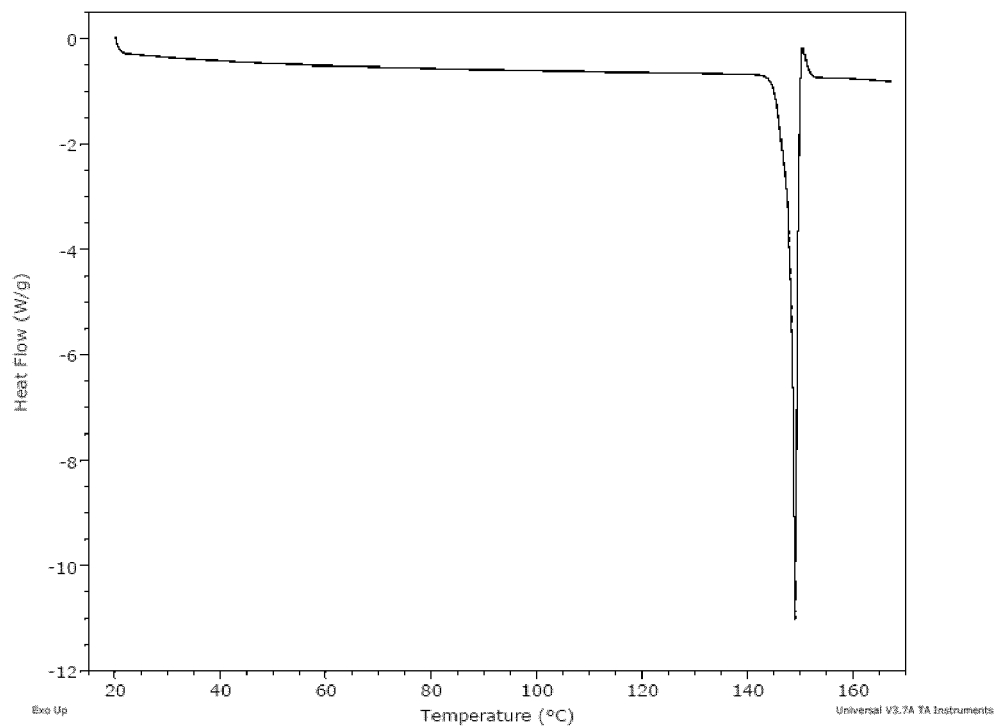
Figure 17:
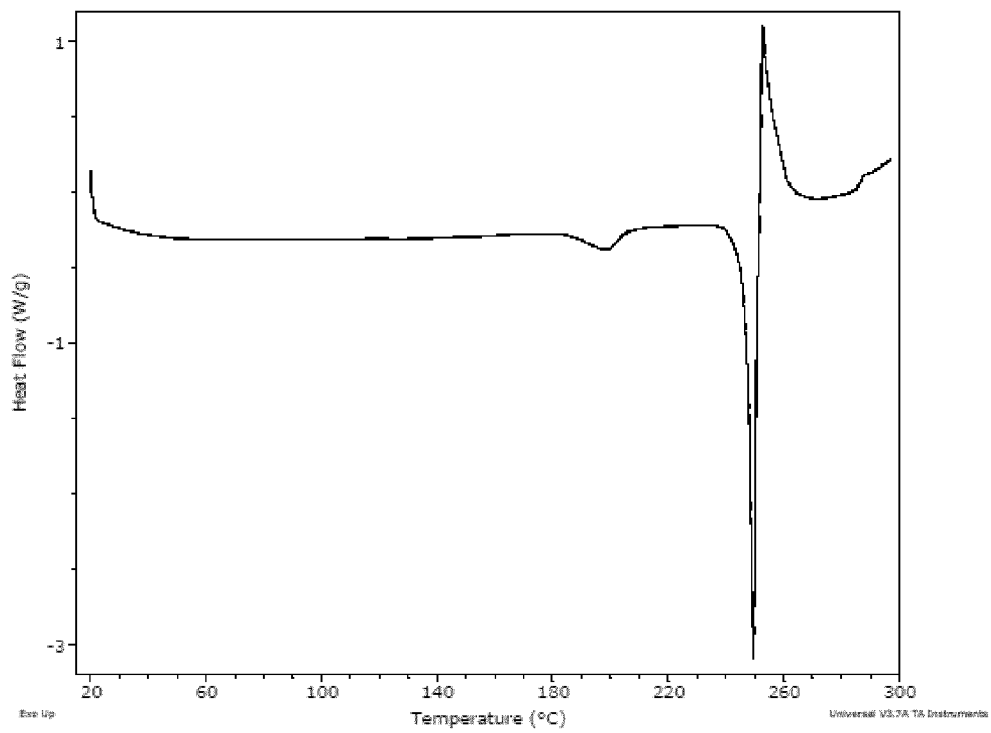
Figure 18:
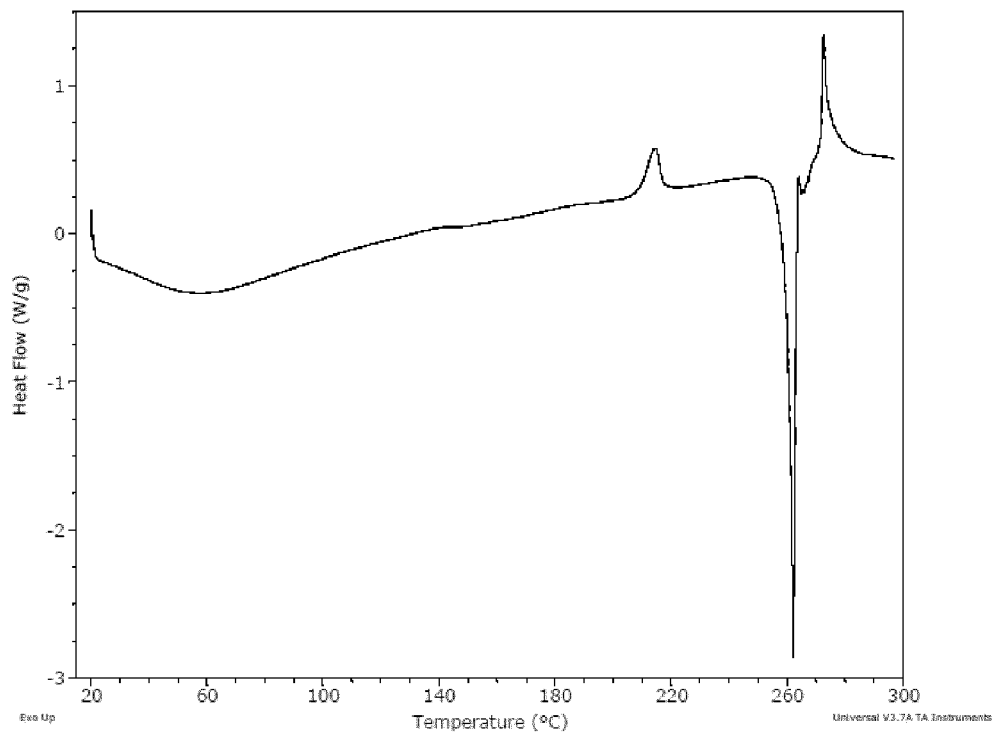
Figure 19:
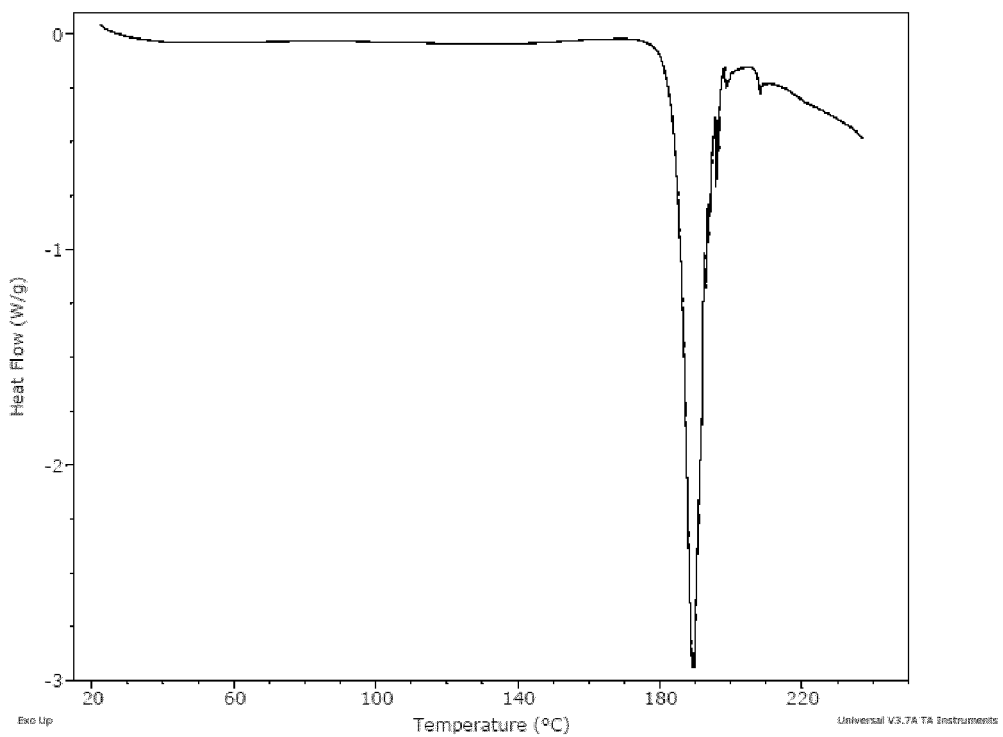
Figure 20:
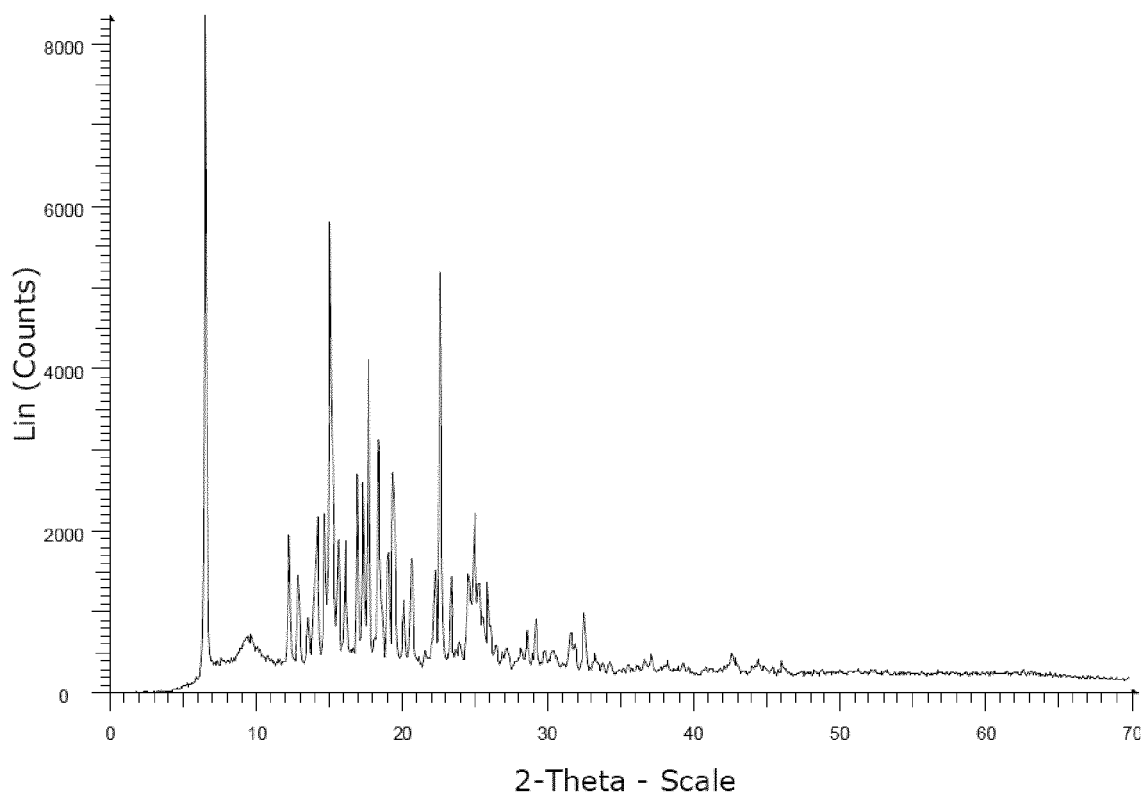
Figure 21:
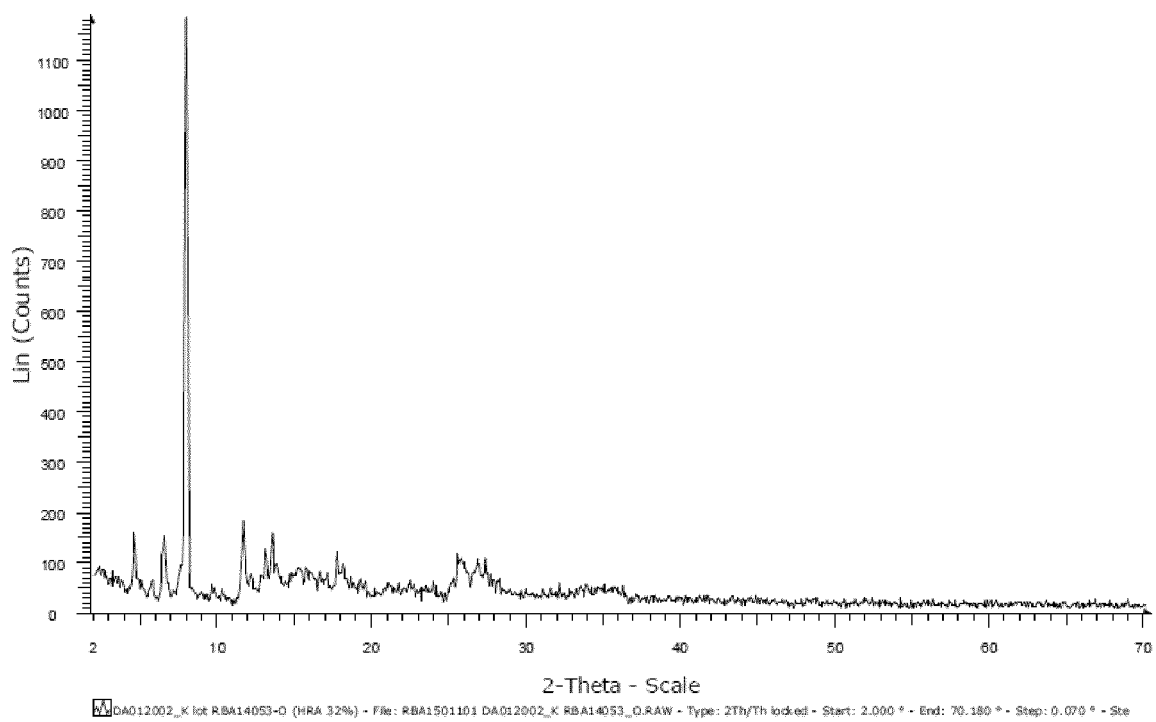
Figure 22:
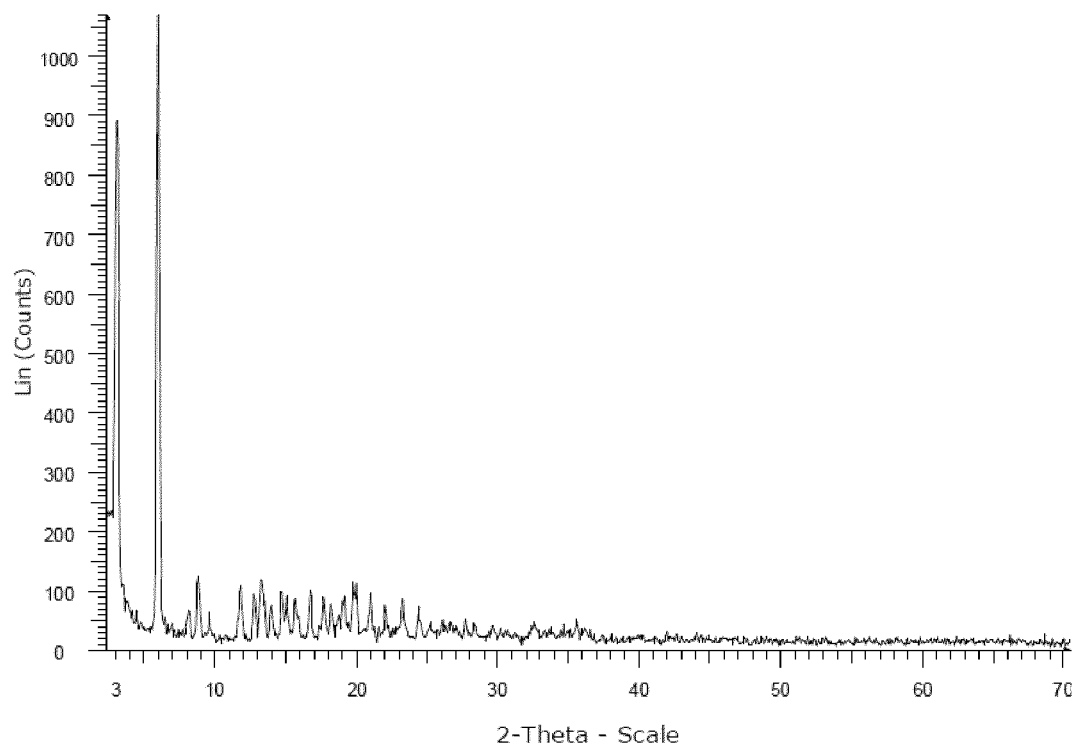
Figure 23:
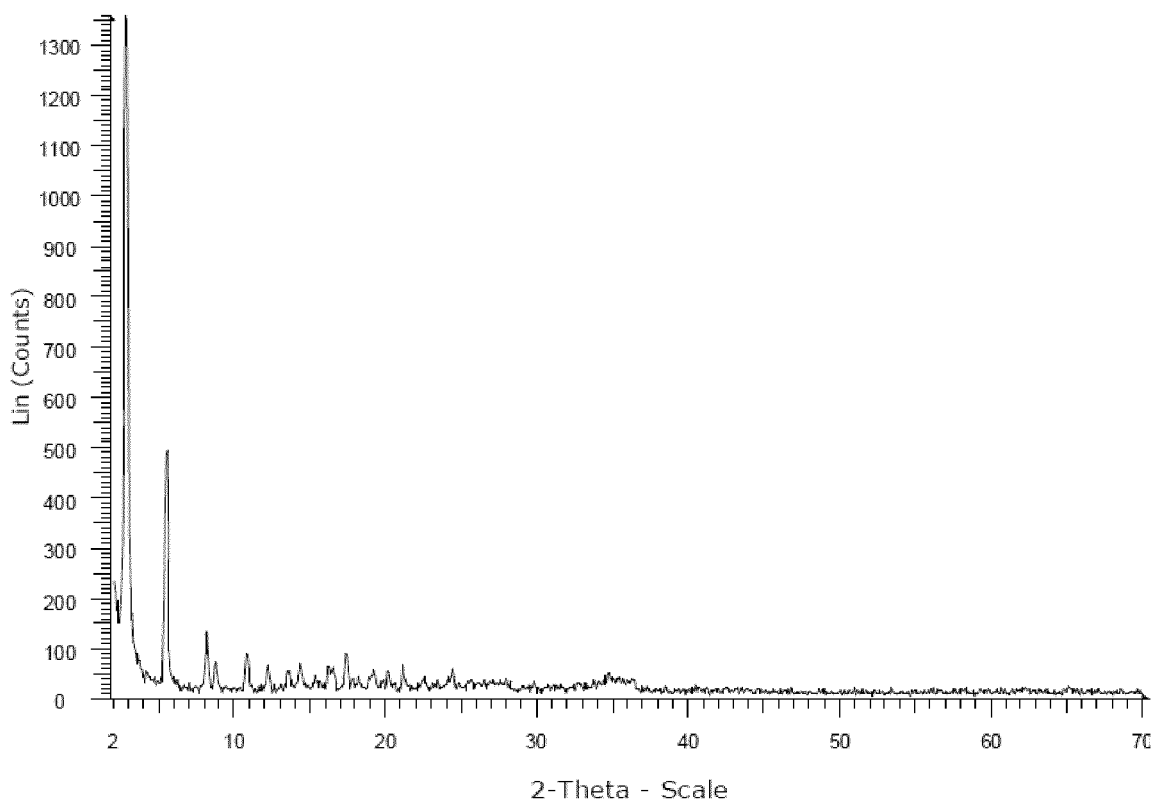
Figure 24:
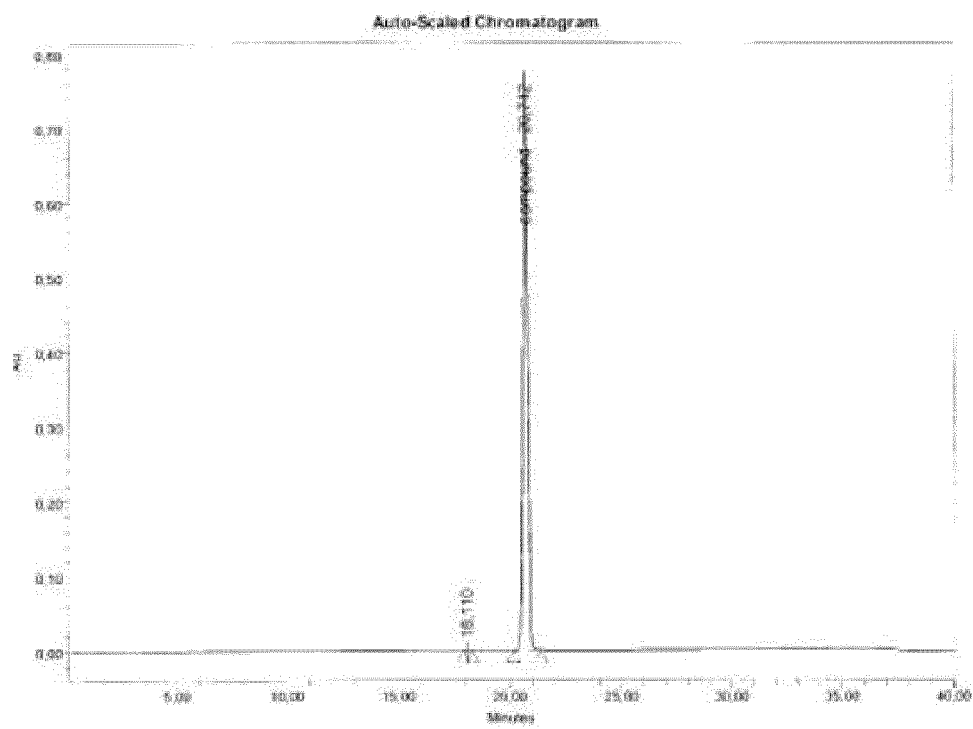
Figure 25:
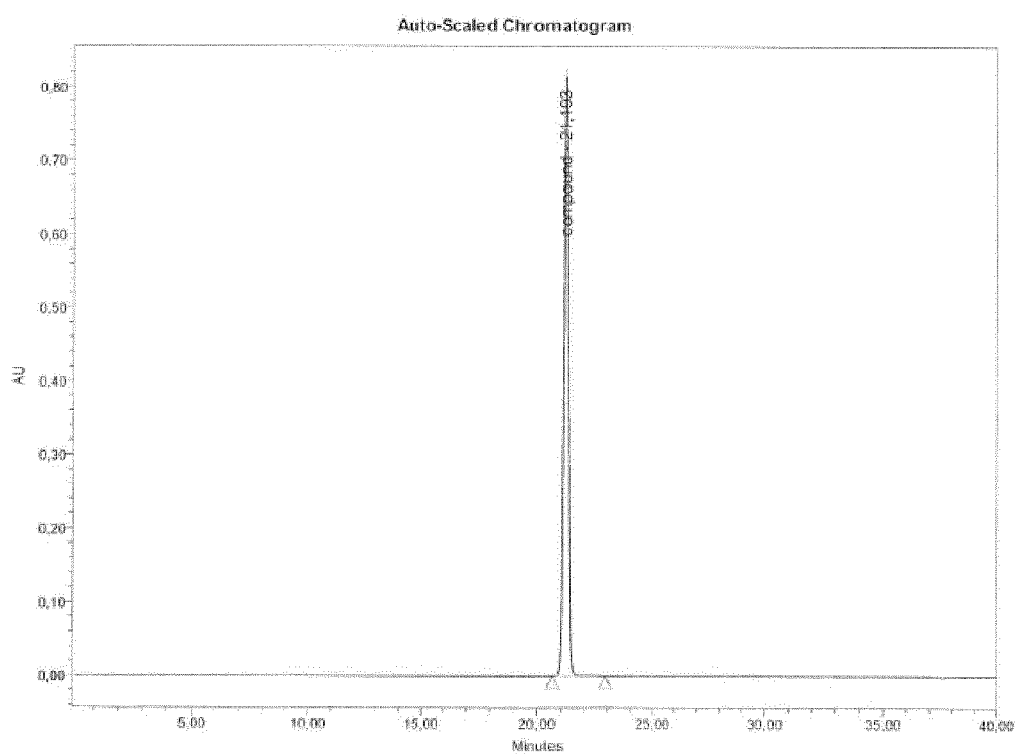
Figure 26:
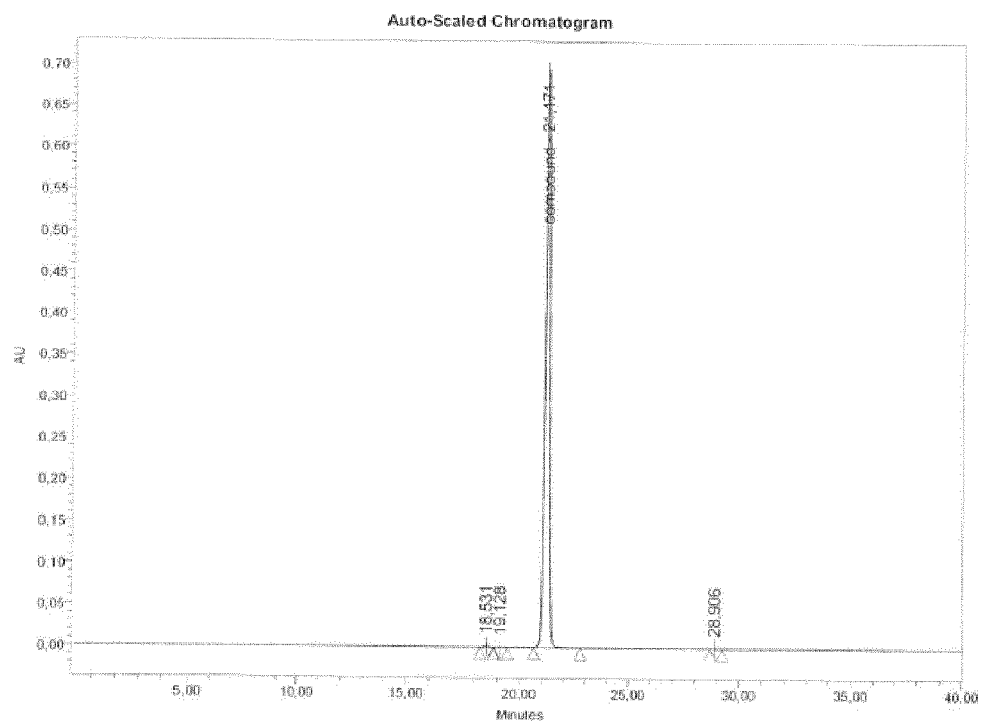
Figure 27:
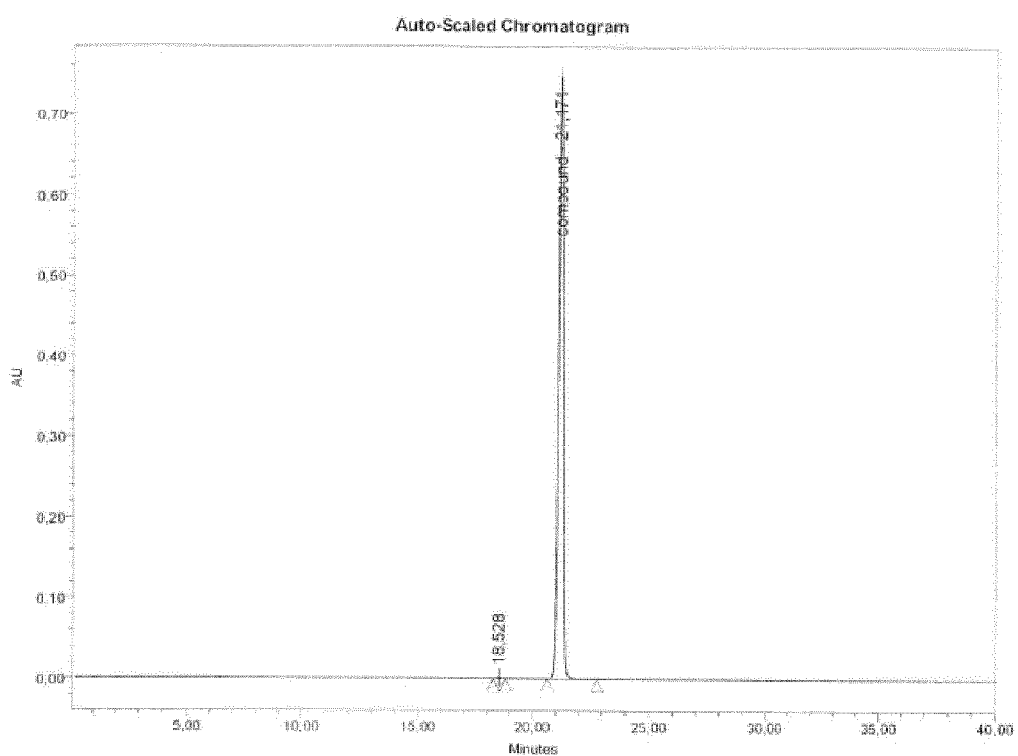
Figure 28:
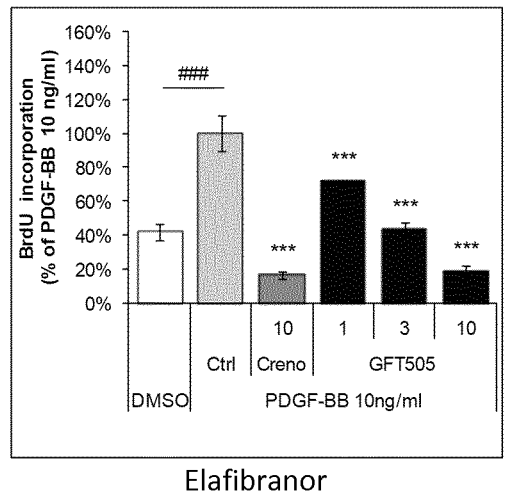
Figure 28:
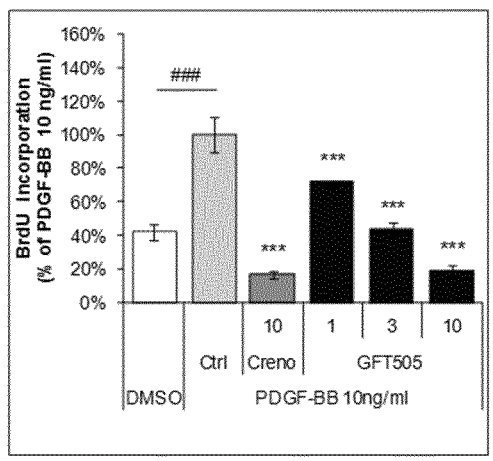
Figure 28:
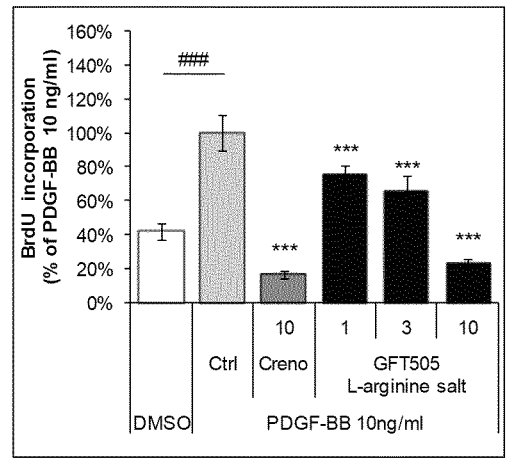
Figure 28:
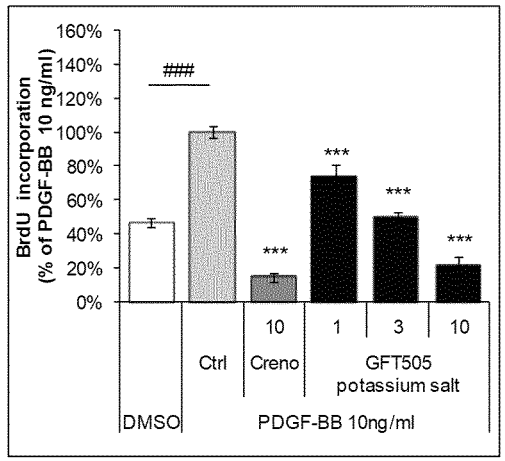
Figure 28:
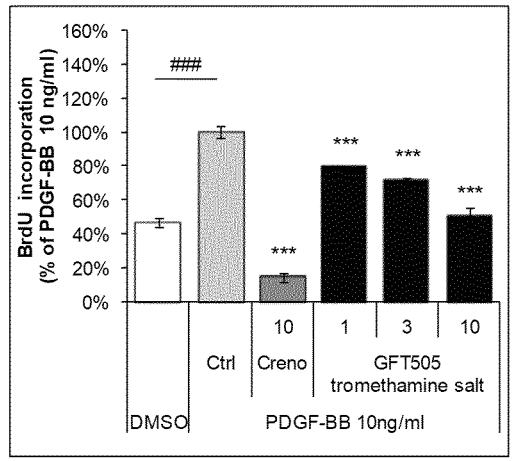
Figure 29:
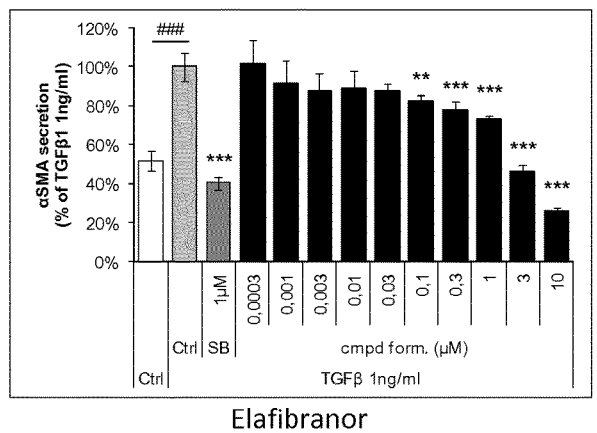
Figure 29:
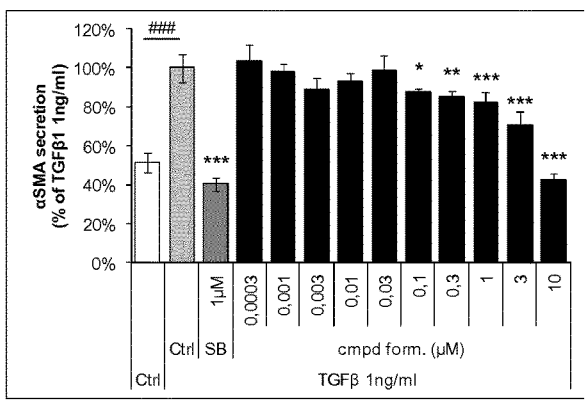
Figure 29:
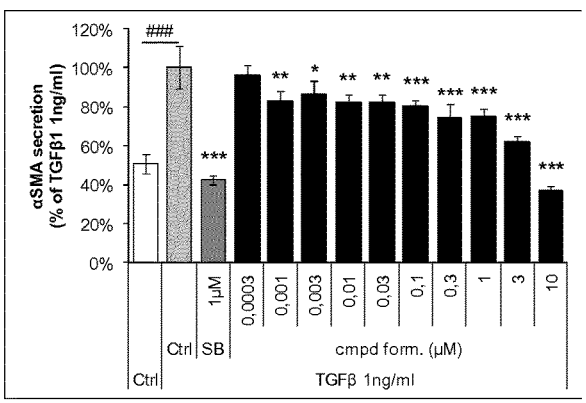
Figure 29:
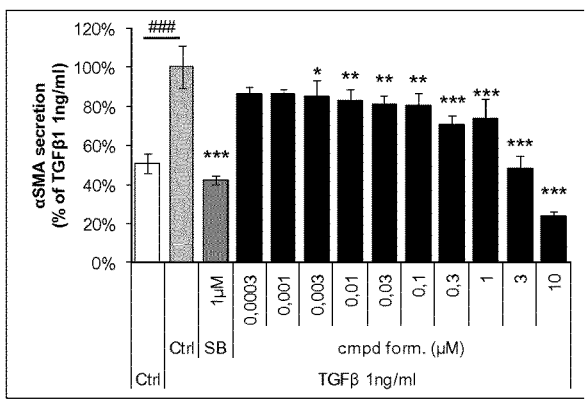
Figure 29:
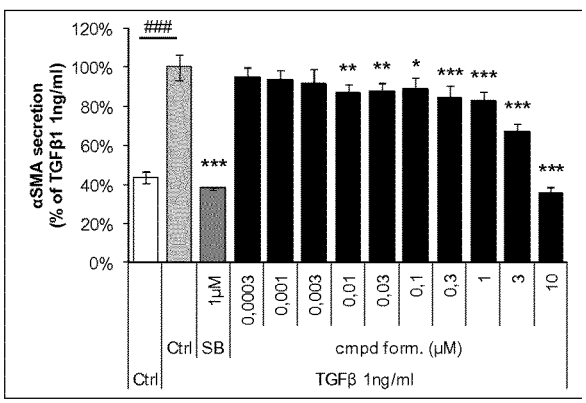
Figure 30:
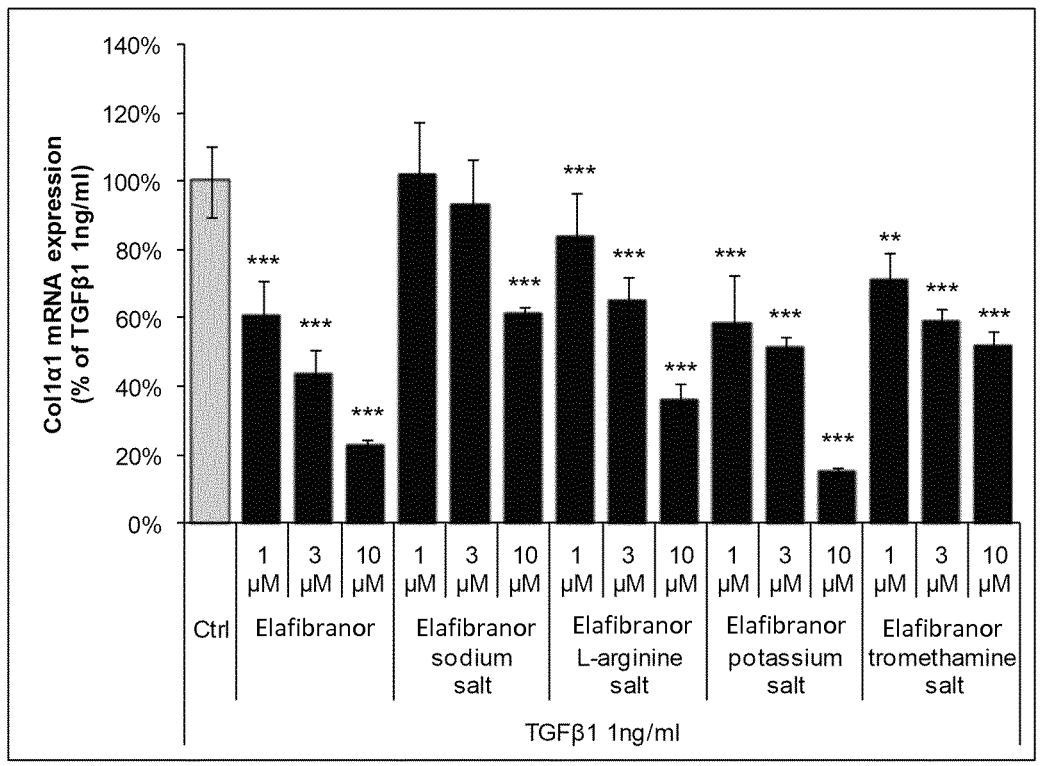
Figure 31:
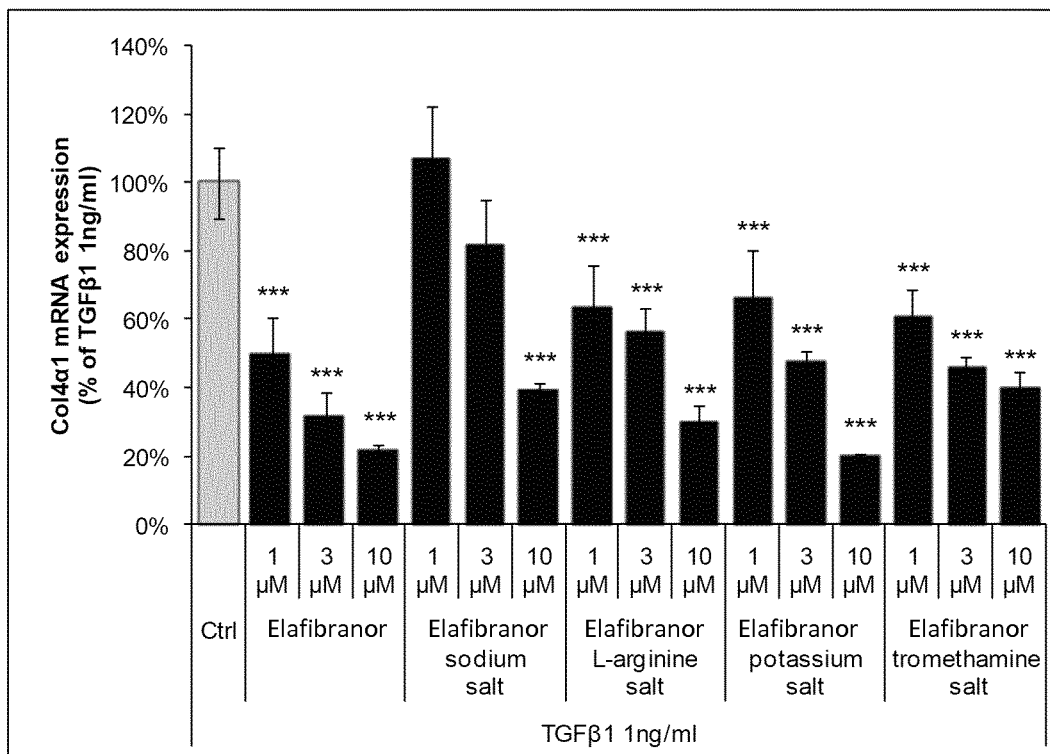

FIG. 10: Optical Microscopy of Salt X
FIG. 10 shows optical microscopy for Salt X re-crystallized in acetone/H₂O under cross-polarized light (Magnification ×84).
FIG. 11: Optical Microscopy of Salt XI
FIG. 11 shows optical microscopy for Salt XI re-crystallized in EtOH/H₂O under cross-polarized light (Magnification ×84).
FIG. 12: Optical Microscopy of Salt XII
FIG. 12 shows optical microscopy for Salt XII re-crystallized in acetone/H₂O under cross-polarized light (Magnification ×84).
FIG. 13: Optical Microscopy of Salt XIII
FIG. 13 shows optical microscopy for Salt XIII re-crystallized in THF/H₂O under cross-polarized light (Magnification ×84).
FIG. 14: Optical Microscopy of Salt XIV
FIG. 14 shows optical microscopy for Salt XIV re-crystallized in H₂O under cross-polarized light (Magnification ×84).
FIG. 15: Optical Microscopy of Salt XV
FIG. 15 shows optical microscopy for Salt XV re-crystallized in H₂O under cross-polarized light (Magnification ×84).
FIG. 16: DSC Thermogram of Salt I
FIG. 16 shows DSC profile at 5° C./min of Salt I
FIG. 17: DSC Thermogram of Salt II
FIG. 17 shows DSC profile at 5° C./min of Salt II
FIG. 18: DSC Thermogram of Salt III
FIG. 18 shows DSC profile at 5° C./min of Salt III
FIG. 19: DSC Thermogram of Salt IV
FIG. 19 shows DSC profile at 5° C./min of Salt IV
FIG. 20: X-Ray Diffraction of Salt I
FIG. 20 shows X-ray diffraction profile of Salt I (crystallized in EtOH/AcEt)
FIG. 21: X-Ray Diffraction of Salt II
FIG. 21 shows X-ray diffraction profile of Salt II (crystallized in CH3CN)
FIG. 22: X-Ray Diffraction of Salt IV
FIG. 22 shows X-ray diffraction profile of Salt IV (crystallized in acetone/H₂O)
FIG. 23: X-Ray Diffraction of Salt IV Dihydrate
FIG. 23 shows X-ray diffraction profile of Salt IV dihydrate (crystallized in acetone/H₂O)
FIG. 24: Chromatographic Profile of Salt I
FIG. 24 shows the HPLC profile of Salt I (crystallized in EtOH/AcEt)
FIG. 25: Chromatographic Profile of Salt II
FIG. 25 shows the HPLC profile of Salt II (crystallized in CH3CN)
FIG. 26: Chromatographic Profile of Salt III
FIG. 26 shows the HPLC profile of Salt III (crystallized in acetone)
FIG. 27: Chromatographic Profile of Salt IV
FIG. 27 shows the HPLC profile of Salt IV (crystallized in acetone/H₂O)
FIG. 28: PDGF-Induced Proliferation of hHSC
FIG. 28 shows that the compounds according to the invention inhibit, in a dose-dependent way, the proliferation of hHSC that was induced by a treatment with PDGF-BB
FIG. 29: Reduction of α-SMA Protein Secretion in TGFβ1-Activated hHSC
FIG. 29 shows that the compounds according to the invention reduce α-SMA protein secretion in TGFβ1-activated hHSC.
FIG. 30: Reduction of COL1A1 Secretion in TGFβ1-Activated hHSC
FIG. 30 shows that the compounds according to the invention reduce COL1A1 secretion in TGFβ1-activated hHSC.
FIG. 31: Reduction of COL4A1 Secretion in TGFβ1-Activated hHSC
FIG. 31 shows that the compounds according to the invention reduce COL4A1 secretion in TGFβ1-activated hHSC.

DETAILED DESCRIPTION OF THE INVENTION

The present invention may be understood more readily by reference to the following detailed description taken in connection with the accompanying figures and examples which form a part this disclosure. It is to be understood that this invention is not limited to the specific products, methods, conditions or parameters described and/or shown herein, and that the terminology used herein is for the purpose of describing particular embodiments by way of example only and is not intended to limit the claimed invention.

The entire disclosures of each patent, patent application, and publication cited or described in this document are herein incorporated by reference.

Unless defined otherwise, all technical and scientific terms used herein have the same meaning as is commonly understood by one of skill in the art to which the present disclosure belongs.

As employed above and throughout the disclosure, the following terms and abbreviations, unless otherwise indicated, shall be understood to have the following meanings.

In the present disclosure, the singular forms "a", "an" and "the" include the plural reference, and reference to a particular numerical value includes at least that particular value, unless the context clearly indicates otherwise. Thus, for example, a reference to "a solvent" is a reference to one or more of such solvents and equivalents thereof to those skilled in the art, and so forth.

As used above, the term "disease" refers to a disease, disorder, condition, symptom, or indication. This term is used interchangeably with the phrase "disease or disorder".

As used herein, the terms "treatment" or "therapy" (as well as different word forms thereof) includes preventative (e.g., prophylactic), curative, or palliative treatment. Such preventative, curative, or palliative treatment may be full or partial. For example, complete elimination of unwanted symptoms, or partial elimination of one or more unwanted symptoms would represent "treatment" as contemplated herein.

As used herein, the phrase "therapeutically effective amount" refers to the amount of active compound that elicits the biological or medicinal response that is being sought in a tissue, system, animal, individual or human by a researcher, veterinarian, medical doctor or other clinician, which includes one or more of the following:
(1) preventing the disease or condition; for example, preventing a disease, condition or disorder in an individual who may be predisposed to the disease, condition or disorder but does not yet experience or display the pathology or symptomatology of the disease;
(2) inhibiting the disease or condition; for example, inhibiting a disease, condition or disorder in an individual who is experiencing or displaying the pathology or symptomatology of the disease, condition or disorder (i.e., including arresting further development of the pathology and/or symptomatology); and (3) ameliorating the disease or condition; for example, ameliorating a disease, condition or disorder in an individual who is experiencing or displaying the pathology or symptomatology of the disease, condition or disorder (i.e., including reversing the pathology and/or symptomatology).

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The present invention provides salts of elafibranor. Although elafibranor is well known among those of ordinary skill in the art in its free acid form, the present disclosure is directed to this molecule in different salt forms. Salts of elafibranor may have advantageous properties including chemical purity, flowability, solubility, morphology or crystal habit, and stability (such as storage stability, stability to dehydration, stability to light, stability to polymorphic conversion, low hygroscopicity, and low content of residual solvents).

The term "purity", when referring to one of the salts of elafibranor disclosed herein, means the degree to which the particular salt form is undiluted or unmixed with another salt and/or degradation by-products and/or extraneous material(s), and is expressed as a percentage by weight (wt %).

The term "purity", when referring to a formulation or dosage form of one of the salt of elafibranor disclosed herein, which formulation or dosage form comprises the particular crystalline form as the active pharmaceutical agent (as well as one or more other materials such as a pharmaceutically acceptable vehicle), means the degree to which the active pharmaceutical agent in the formulation or dosage form comprises that particular salt and no other salt(s) of elafibranor, and is also expressed as a percentage by weight (wt %).

Since the weight percent of a particular salt can vary with measurements taken by different instruments, different calibrations and/or different software packages, those skilled in the art will appreciate that any measured purity level will show some variability. Due to these sources of variability, it is common to recite purity using the word "about" or "at least" when referring to the percent purity of a salt form. In a particular embodiment, "about" refers to a variation of a numerical value of plus or minus 10%, in particular of plus or minus 5%.

The existence of various salts of the compound has been explored in order to determine the most appropriate form of the compound for the proposed use.

Novel salts of the compound of formula (I) have now been synthesized and characterized. Some of the novel salts have very good stability, facilitating their use in the preparation of pharmaceutical dosage forms.

During salt studies, inventors discovered a list of salt-hits of interest, i.e. list of the pharmaceutically acceptable counter-ions that are the most likely to form salts when associated to elafibranor.

Fifteen different salts of elafibranor are disclosed herein. The list of tested bases is presented in TABLE 1.

Counter-ions may be selected from the following the non-exhaustive list: ammonia, L-arginine, benethamine, benzathine, tert-butylamine (erbumine), calcium hydroxide, choline hydroxide, deanol, diethanolamine (2,2'-iminobis(ethanol), diethylamine, epolamine (1-(2-hydroxyethyl)pyrrolidine), 2-(diethylamino)-ethanol, ethanolamine (2-aminoethanol), ethylenediamine, glycine, hydrabamine, 1H-imidazole, L-Lysine, magnesium hydroxide, meglumine (N-methyl-glucamine), 4-(2-hydroxyethyl)-morpholine, piperazine, potassium hydroxide, sodium hydroxide, triethanolamine (2,2',2"-nitrilo-tris(ethanol)), tromethamine, zinc hydroxide, in particular tromethamine, potassium, sodium, benethamine, benzathine, L-arginine, ethanolamine, meglumine, glycine, erbumine, L-lysine, epolamine, choline, preferably tromethamine, potassium, sodium, benethamine, benzathine, L-arginine, more preferably tromethamine, potassium, sodium, L-arginine, more particularly tromethamine. In particular embodiments, the invention relates to an ammonia, L-arginine, benethamine, benzathine, tert-butylamine (erbumine), calcium, choline, deanol, diethanolamine (2,2'-iminobis(ethanol), diethylamine, epolamine (1-(2-hydroxyethyl)pyrrolidine), 2-(diethylamino)-ethanol, ethanolamine (2-aminoethanol), ethylenediamine, glycine, hydrabamine, 1H-imidazole, L-Lysine, magnesium, meglumine (N-methyl-glucamine), 4-(2-hydroxyethyl)-morpholine, piperazine, potassium, sodium, triethanolamine (2,2',2"-nitrilo-tris(ethanol)), tromethamine or zinc salt of elafibranor.

In a further particular embodiment, the salt of elafibranor is selected from a tromethamine, potassium, sodium, L-arginate, benethamine, benzathine, ethanolamine, meglumine, glycine, erbumine, L-lysine, choline, epolamine, magnesium or 2-amino-2-methyl-propan-1-ol salt of elafibranor. In yet another embodiment, the salt of elafibranor is selected from tromethamine, potassium, sodium and L-arginate elafibranor salts. In another embodiment, the salt of elafibranor is selected from tromethamine, potassium and L-arginate elafibranor salts. In a further embodiment, the salt of elafibranor is the tromethamine salt of elafibranor.

In another embodiment, the elafibranor salt is selected from the following salts I to XV, that may be in crystalline form:

I. Crystalline elafibranor tromethamine salt (salt I) has a X-ray diffraction pattern comprising the following diffraction peaks (2θ in angular degrees ±0.2°): 6.5°, 12.2°, 15.0°, 15.3°, 16.9°, 17.3°, 17.6°, 18.4°, 19.4°, and 22.6°.

Elafibranor tromethamine salt (salt I) has a melting point, by Differential Scanning calorimetry, of 148° C. at a heating rate of 5° C./min.

II. Crystalline elafibranor potassium salt (salt II) has a X-ray diffraction pattern comprising the following diffraction peaks (2θ in angular degrees ±0.2°): 4.6°, 8.0°, 11.7°, 13.1°, and 13.6°.

Elafibranor potassium salt (salt II) has a melting point, by Differential Scanning calorimetry, of 247° C. at a heating rate of 5° C./min.

III. Elafibranor sodium salt (salt III), which has a melting point, by Differential Scanning calorimetry, of 261° ° C. at a heating rate of 5° C./min.

IV. Crystalline elafibranor L-arginate salt (salt IV) has a X-ray diffraction pattern comprising the following diffraction peaks (2θ in angular degrees ±0.2°): 3°, 5.9°, 8.8°, 11.7°, 13.2°, 19.8°, and 19.9°.

Elafibranor L-arginate salt (salt IV) has a melting point, by Differential Scanning calorimetry, of 167° C. at a heating rate of 5° C./min.

V. Elafibranor benethamine salt (salt V) has a melting point, by Differential Scanning calorimetry, of 125-158° C. at a heating rate of 5° C./min, corresponding to a melting of a polycrystalline cluster.

VI. Elafibranor benzathine salt (salt VI) has a melting point, by Differential Scanning calorimetry, of 138-

148° C. at a heating rate of 5° C./min, corresponding to a melting of rods and polycrystalline cluster.

VII. Elafibranor ethanolamine salt (salt VII) has a melting point, by Differential Scanning calorimetry, of 118-160° C. at a heating rate of 5° C./min, corresponding to a melting of equants.

VIII. Elafibranor meglumine salt (salt VIII) has, by Differential Scanning calorimetry at a heating rate of 5° C./min, a first melting at 35-88° C. then a second melting at 133-158° C., corresponding to melting two polycrystalline clusters.

IX. Elafibranor glycine salt (salt IX) has, by Differential Scanning calorimetry at a heating rate of 5° C./min, a first melting at 148-188° C. corresponding to melting of equants, then a second melting at 178-223° C., corresponding to melting strands/laths.

X. Elafibranor erbumine salt (salt X) has a melting point, by Differential Scanning calorimetry, of 148-161° C. at a heating rate of 5° C./min, corresponding to a melting of polycrystalline cluster.

XI. Elafibranor L-lysine salt (salt XI) has a melting point, by Differential Scanning calorimetry, of 104-162° C. at a heating rate of 5° C./min, corresponding to a melting of polycrystalline cluster.

XII. Elafibranor choline salt (salt XII) has a melting point, by Differential Scanning calorimetry, of 116-159° C. at a heating rate of 5° C./min, corresponding to a melting of polycrystalline cluster.

XIII. Elafibranor epolamine salt (salt XIII) has a melting point, by Differential Scanning calorimetry, of 108-158° C. at a heating rate of 5° C./min, corresponding to a melting of polycrystalline cluster.

XIV. Elafibranor magnesium salt (salt XIV). Magnesium salt shows a melting point of 142-162° C. corresponding to the melting of a polycrystalline cluster followed by a the melting of sticks (163-215° C.).

XV. Elafibranor 2-amino-2-methyl-propan-1-ol salt (salt XV). Salt XV has a melting point of 138-161° C. corresponding to the melting of equants and platelets.

In another embodiment, the elafibranor salt is selected from the salts I to XV, tromethamine, potassium and L-arginate elafibranor salts in crystalline form. In a further embodiment, the salt of elafibranor is the tromethamine salt of elafibranor, in crystalline form.

Differential scanning calorimetry, or DSC, is a thermoanalytical technique in which the difference in the amount of heat required to increase the temperature of a sample and reference is measured as a function of temperature. DSC data shows differential heat flow plotted against temperature. As a sample undergoes a thermal event, it is effectively altering the heat flow due to the latent heat associated with the thermal event, which is then reflected as a peak or a shift in baseline. DSC can be used to characterize thermal properties of crystalline forms, such as melting temperature or heat of fusion. Therefore, the melting points of the salts of elafibranor disclosed herein can be characterized by DSC.

Single-crystal X-ray diffraction provides three-dimensional structural information about the positions of atoms and bonds in a crystalline form. It is not always possible or feasible, however, to obtain such a structure from a crystalline form due to, for example, insufficient crystal size or difficulty in preparing crystals of sufficient quality for single-crystal X-ray diffraction. Structural identification information can, however, be obtained from other solid-state techniques such as X-ray powder diffraction and Raman spectroscopy. These techniques are used to generate data on a solid crystalline form. Once that data has been collected on a known crystalline form, that data can be used to identify the presence of that crystalline form in other materials. Thus, these data effectively characterize the crystalline form. For example, a X-ray powder diffraction pattern, or a portion thereof, can serve as a fingerprint which characterizes a crystalline form. A X-ray powder diffraction plot is an x-y graph with scattering angles 2θ (diffraction) on the x-axis and intensity on the y-axis. The peaks within this plot can be used to characterize a crystalline form. Although the peaks within an entire diffractogram can be used to characterize a crystalline form, a subset of the more characteristic peaks can also be used to accurately characterize a crystalline form. The data is often represented by the position of the peaks on the x-axis rather than the intensity of peaks on the y-axis because peak intensity may vary with sample orientation. There is also variability in the position of peaks on the x-axis. There are several sources of this variability, one of which comes from sample preparation.

Samples of the same crystalline material prepared under different conditions may yield slightly different diffractograms. Factors such as particle size, moisture content, solvent content, and orientation can affect how a sample diffracts X-rays. Another source of variability comes from instrument parameters. Different X-ray instruments operate using different parameters and these may lead to slightly different diffraction patterns from the same crystalline form. Likewise, different software packages process X-ray data differently and this also leads to variability. These and other sources of variability are known to those of ordinary skill in the art. Due to these sources of variability, it is common to recite X-ray diffraction peaks using the word "about" prior to the peak value in 2θ. The word "about" incorporates this variability which under most sampling conditions, and most data collection and data processing conditions, leads to a variability in peak position of about plus or minus 0.2 scattering angle (2θ). Thus, when a peak is said to be at about 10.5 scattering angle (2θ), under most sampling, data collection, and data processing conditions, that peak will appear anywhere between 10.3 (2θ) and 10.7 (2θ).

High-performance liquid chromatography, or HPLC, is a chromatographic technique used to separate the compounds in a mixture, to identify each compound, and to quantify each compound. HPLC is a technique known in the art to determine the purity of a compound. The purity of salts I to XV of elafibranor can be determined using HPLC as is well known to those of ordinary skill in the art.

In a preferred embodiment of the invention, the salts I to XV are substantially free of impurities. By "substantially free", it is meant in the present invention that salts I to XV comprise less than 10%, preferably less than 5% and more preferably less than 2% impurity or impurities, even more preferably less than 1% impurity or impurities.

In certain embodiments, the substantial absence of impurities means the substantial absence of extraneous matter, such as a salt forming acid, residual solvents, or any other impurities that may result from the preparation, and/or isolation of elafibranor.

The inventors have obtained salt forms of the compound with the following chromatographic purity by percentage area measured at 350 nm:

The salt I has a purity of 99.9%.
The salt II has a purity of 100%.
The salt III has a purity of 99.7%.
The salt IV has a purity of 99.8%.

A further aspect of the present invention provides methods for producing substantially pure salts of elafibranor. The phrase "substantially pure", as used herein, means that the salt has a purity of about 90% by weight, preferably about 95% by weight and more preferably about 98% by weight.

In general, in some embodiments, the method for preparing a substantially pure salts I to XV of elafibranor comprises contacting elafibranor with a solvent to form a saturated or a near saturated solution. Thus, all crystal forms disclosed here were prepared by dissolving elafibranor in different types of solvent during a maturation step. Some salts may be obtained after a recrystallisation step.

The solvent used in the methods may vary. In particular, the solvent may be a protic solvent, an aprotic solvent, or combinations thereof. Elafibranor that is contacted with the solvent may be in a solid form (e.g. a powder) or a liquid form (e.g. in a solution comprising a co-solvent, or a concentrated oil/gel/gum). The temperature of the method may also vary.

In a particular embodiment of the invention, the dissolutions are done away from light.

In some embodiments, the salt of elafibranor, such as a salt selected from salts I-XV, is at least partially solvated, such as partially hydrated. In other embodiments, the salt of elafibranor, such as a salt selected from salts I-XV, is not solvated, the salt being in particular anhydrous.

According to a particular embodiment of the invention, the salts I, II, III and IV are preferred. According to a further embodiment, salts I, II and IV in crystalline form are preferred According to another embodiment, the invention relates to the tromethamine salt of elafibranor (salt I). In another embodiment, the invention relates to the tromethamine salt of elafibranor (salt I) in crystalline form.

Another aspect of the present invention relates to a pharmaceutical composition comprising a salt of elafibranor, such as a salt described above, in particular a salt selected from salts I-XV.

In a particular embodiment, the pharmaceutical composition comprises salt I, salt II, salt III or salt IV. In yet another particular embodiment, the pharmaceutical composition comprises salt I, salt II or salt IV, in crystalline form.

In a more particular embodiment, the pharmaceutical composition comprises salt I.

The pharmaceutical composition may comprise the salt of elafibranor in any of the embodiments described above, and a pharmaceutically acceptable excipient.

The pharmaceutical composition includes a therapeutically effective amount of the salt of elafibranor.

The present compositions may be formulated for any type of administration. For example, the compositions may be formulated for administration orally, topically, parenterally, enterally, or by inhalation. The salt of elafibranor may be formulated for neat administration, or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavoring agent, or printing ink. Any material used in preparing any dosage unit form is preferably pharmaceutically pure and substantially non-toxic in the amounts employed.

In addition, the salt of elafibranor may be incorporated into sustained-release preparations and formulations. Administration in this respect includes administration by, inter alia, the following routes: oral; intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients, for example, for oral, topical, or parenteral administration, include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the salt of elafibranor in the pharmaceutically appropriate amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and freeze drying techniques that yield a powder of the active ingredient or ingredients, plus any additional desired ingredient from the previously sterile-filtered solution thereof.

Also disclosed are methods of producing such pharmaceutical compositions comprising combining a salt of elafibranor with a pharmaceutically acceptable excipient. Any acceptable method of combining an active agent with a pharmaceutically acceptable excipient may be used in accordance with the present methods, and those of ordinary skill in the art can readily appreciate appropriate techniques of combination. In some embodiments, the step of combination may be as simple as adding a desired quantity of the salt of elafibranor to an existing substance, such as a liquid beverage or a powdered beverage mixture. In other embodiments, the step of combination includes any technique that is conventionally used to mix active agents with excipients pursuant to preparing a pharmaceutical dosage form (for example, solid, semi-solid, liquid, or in a form suitable for inhalation), a cosmetic item (such as a powder, cream, lotion, or emollient), or a food item (for example, solid, semi-solid, or liquid).

In other aspects, the present disclosure provides a therapeutic method for the treatment of a disease in a subject in need thereof, comprising administering to said subject a salt of elafibranor. The administration of the salt of elafibranor may be by any of the routes described above in connection with the present pharmaceutical compositions.

The subject is a mammalian subject, preferably a human subject. However, the subject may also be any animal, including a laboratory animal. Thus, as can be readily appreciated by one of ordinary skill in the art, the salts, crystalline forms and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, and the like, avian species, such as chickens, turkeys, songbirds, and the like, i.e., for veterinary medical use.

The salts of the present invention may be used in methods for treating a number of diseases or conditions. In particular, the salt of elafibranor of the present invention is administered to a subject in need thereof for the treatment of any disease or condition disclosed in WO 2004/005233, WO 2004/005243, WO 2011/064350 or WO 2014/111584.

In particular, the salt of elafibranor is useful for the treatment of diseases such as immune, inflammatory, metabolic, fibrotic and cholestatic diseases. In a particular embodiment, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, keloid, old myocardial infarction, scleroderma/systemic sclerosis, inflammatory diseases, neurodegenerative diseases, cancers, liver cancer, hepatocellular carcinoma, gastrointestinal cancer, gastric cancer, meningioma associated with neurofibromatosis, pancreatic neuroendocrine tumors, pancreatic exocrine tumors, leukemia, myeloproliferative/myelodisplastic diseases, mastocytosis, dermatofibrosarcoma, solid tumors including breast, lung, thyroid or colorectal cancer, a prostate cancer, liver fibrosis or cirrhosis of any origin, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, skin fibrosis, epidermis fibrosis, endodermis fibrosis, skin fibrosis due to scleroderma/systemic sclerosis, lung fibrosis, lung fibrosis consecutive to chronic inflammatory airway diseases, such as COPD, asthma, emphysema, smoker's lung fibrosis, tuberculosis, pulmonary fibrosis, idiopathic pulmonary fibrosis (IPF), heart fibrosis, kidney fibrosis, nephrogenic systemic fibrosis, muscle fibrosis, soft tissue (e.g. mediastinum or retroperitoneum) fibrosis, bone marrow fibrosis, joint fibrosis, tendon fibrosis, cartilage fibrosis, pancreas fibrosis, uterus fibrosis, nervous system fibrosis, testis fibrosis, ovary fibrosis, adrenal gland fibrosis, artery fibrosis, vein fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, peri-implantational fibrosis and asbestosis, arthrofibrosis, adhesive capsulitis.

In a particular embodiment, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, liver cancer, hepatocellular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, lung fibrosis, lung fibrosis consecutive to chronic inflammatory airway diseases, such as COPD, asthma, emphysema, smoker's lung fibrosis, tuberculosis, pulmonary fibrosis, idiopathic pulmonary fibrosis (IPF), In a further aspect, the salt of elafibranor is used for the inhibition of proliferation and/or activation of fibroblasts responsible for the production of collagen fibers and/or responsible for the production of the extracellular matrix.

According to the present invention, the term "autoimmune diseases" is used to designate a condition that arises from an abnormal immune response of the body against substances and tissues normally present in the body. The disease may be restricted to certain organs (e.g. in type I diabetes or autoimmune thyroiditis) or involve a particular tissue in different places (e.g. in Goodpasture's disease, affection of the basement membrane in the lung and the kidney).

The term "inflammation" is used to designate a condition that arise from a protective response involving host cells, blood vessels, and proteins and other mediators which may serve to eliminate the cause of cell/tissue injury, as well as the necrotic cells/tissues resulting from the original insult, and to initiate the process of repair. The inflammatory reaction may be manifested by pain, heat, redness, swelling, blood vessels dilatation, blood flow increase and loss of function.

According to the present invention, the terms "fibrosis", "fibrotic disease", "fibrotic disorder" and declinations thereof denote a pathological condition of excessive deposition of fibrous connective tissue in an organ or tissue. More specifically, fibrosis is a pathological process, which includes a persistent fibrotic scar formation and overproduction of extracellular matrix by the connective tissue, as a response to tissue damage. Physiologically, the deposit of connective tissue can obliterate the architecture and function of the underlying organ or tissue.

According to the present invention, the fibrosis or fibrotic disorder may be associated with any organ or tissue fibrosis. Illustrative, non-limiting examples of particular organ fibrosis include liver, gut, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, soft tissue (e.g. mediastinum or retroperitoneum), bone marrow, joint or stomach fibrosis, in particular liver, kidney, skin, epidermis, endodermis, muscle, tendon, cartilage, heart, pancreas, lung, uterus, nervous system, testis, ovary, adrenal gland, artery, vein, colon, intestine (e.g. small intestine), biliary tract, soft tissue (e.g. mediastinum or retroperitoneum), bone marrow, joint, eye or stomach fibrosis.

According to the present invention, the terms "cholestasis" or "cholestatic disease", or "cholestatic disorder" and declinations thereof denote a pathological condition defined by a decrease in bile flow due to impaired secretion by hepatocytes or to obstruction of bile flow through intra-or extrahepatic bile ducts. Therefore, the clinical definition of cholestasis is any condition in which substances normally excreted into bile are retained.

In a particular embodiment, the fibrotic disorder is selected in the group consisting of a liver, gut, lung, heart, kidney, muscle, skin, soft tissue (e.g. mediastinum or retroperitoneum), bone marrow, intestinal, and joint (e.g. knee, shoulder or other joints) fibrosis.

In a particular embodiment, the fibrotic disorder is selected in the group consisting of liver, lung, skin, kidney and intestinal fibrosis.

In a more particular embodiment of the present invention, treated fibrotic disorder is selected in the group consisting of the following non exhaustive list of fibrotic disorders: non-alcoholic steatohepatitis (NASH), pulmonary fibrosis, idiopathic pulmonary fibrosis, skin fibrosis, eye fibrosis (such as capsular fibrosis), endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, lung fibrosis consecutive to chronic inflammatory airway disease (COPD, asthma, emphysema, smoker's lung, tuberculosis), alcohol or drug-induced liver fibrosis, liver cirrhosis, infection-induced liver fibrosis, radiation or chemotherapeutic-induced fibrosis, nephrogenic systemic fibrosis, Crohn's disease, ulcerative colitis, keloïd, old myocardial infarction, scleroderma/systemic sclerosis, arthrofibrosis, some forms of adhesive capsulitis, chronic fibrosing cholangiopathies such as Primary Sclerosing Cholangitis (PSC) and Primary Biliary Cholangitis (PBC), biliary atresia, progressive familial intrahepatic cholestasis type 3 (PFIC3), peri-implantational fibrosis and asbestosis.

Cholestasis is defined as a decrease in bile flow due to impaired secretion by hepatocytes (hepato-cellular cholestasis) or to obstruction of bile flow through intra-or extra-hepatic bile ducts (obstructive cholestasis). In clinical practice, cholestasis is any condition in which the flow of bile from the liver is slowed or blocked. According to a particular embodiment of the invention, the cholestatic disease is selected in the group consisting of primary biliary cholangitis (PBC), primary sclerosing cholangitis (PSC), Intrahepatic Cholestasis of Pregnancy, Progressive Familial Intrahepatic Cholestasis, Biliary atresia, Cholelithiasis, Infectious Cholangitis, Cholangitis associated with Langerhans cell histiocytosis, Alagille syndrome, Non syndromic ductal paucity, Drug-induced cholestasis, and Total parenteral nutrition-associated cholestasis. In a preferred embodiment, the cholestatic disease is PBC or PSC, in particular PBC.

Examples of inflammatory diseases, fibrotic diseases, metabolic diseases and cholestatic diseases include metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, keloid, old myocardial infarction, scleroderma/systemic sclerosis, inflammatory diseases, neurodegenerative diseases, cancers, liver cancer, hepatocellular carcinoma, gastrointestinal cancer, gastric cancer, meningioma associated with neurofibromatosis, pancreatic neuroendocrine tumors, pancreatic exocrine tumors, leukemia, myeloproliferative/myelodisplastic diseases, mastocytosis, dermatofibrosarcoma, solid tumors including breast, lung, thyroid or colorectal cancer, a prostate cancer, liver fibrosis or cirrhosis of any origin, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, skin fibrosis, epidermis fibrosis, endodermis fibrosis, skin fibrosis due to scleroderma/systemic sclerosis, lung fibrosis, lung fibrosis consecutive to chronic inflammatory airway diseases, such as COPD, asthma, emphysema, smoker's lung fibrosis, tuberculosis, pulmonary fibrosis, idiopathic pulmonary fibrosis (IPF), heart fibrosis, kidney fibrosis, nephrogenic systemic fibrosis, muscle fibrosis, soft tissue (e.g. mediastinum or retroperitoneum) fibrosis, bone marrow fibrosis, joint fibrosis, tendon fibrosis, cartilage fibrosis, pancreas fibrosis, uterus fibrosis, nervous system fibrosis, testis fibrosis, ovary fibrosis, adrenal gland fibrosis, artery fibrosis, vein fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, peri-implantational fibrosis and asbestosis, arthrofibrosis, adhesive capsulitis.

In particular, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, liver cancer, hepatocellular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, lung fibrosis, lung fibrosis consecutive to chronic inflammatory airway diseases, such as COPD, asthma, emphysema, smoker's lung fibrosis. The subjects to be treated according to the invention can be selected on the basis of several criteria associated to inflammatory, metabolic, fibrotic and cholestatic diseases such as previous drug treatments, associated pathologies, genotype, exposure to risk factors, viral infection, as well as any other relevant biomarker that can be evaluated by means of imaging methods and immunological, biochemical, enzymatic, chemical, or nucleic acid detection method.

The invention is further described by reference to the following examples which set forth in detail the preparation of salt forms of the present invention.

Examples

Analysis

HPLC Method

HPLC analyses were performed on a Water column Waters, column Phenomenex Synergi Polar-RP, 4.6×150 mm. TABLE 1 displays the HPLC parameters used to analyze salt samples, in particular determine the parent content to confirm stoichiometry.

TABLE 1

HPLC conditions

| | | |
|---|---|---|
| HPLC system | Injector/Pump: Alliance 2695 Waters | |
| | Detector: Photo Diode Array 996 Waters | |
| | Software: Millennium32 (version 3.20 or 4.0) Waters | |
| Column | Phenomenex Synergi Polar-RP | |
| | 150 mm × 4.6 mm – dp = 4 µm | |
| Mobile phase | A: H2O/TFA 0.05% | |
| | B: MeOH/TFA 0.01% | |

| Time (min) | A % | B % |
|---|---|---|
| 0 | 40 | 60 |
| 2 | 40 | 60 |
| 35 | 5 | 95 |
| 35.1 | 40 | 60 |
| 40 | 40 | 60 |

| | |
|---|---|
| Flow rate | 1 mL/min |
| Column Temperature | 25° C. |
| Detection | UV: $\lambda$ = 350 nm |
| Test solution | Suitable dilution in MeOH |
| | 2 independent assays were performed |
| Injection volume | 20 µL |
| Injector temperature | 20° C. |

TABLE 1-continued

HPLC conditions

| | |
|---|---|
| Standard solution | T 100%: ≈5 mg of Elafibranor free acid qs 50 mL with MeOH |
| | 2 independent standard solutions were performed |
| | Retention time ≈20.8 min for Elafibranor |
| Standard solution | From 5 ug/mL to 100 ug/mL of Elafibranor free acid in MeOH |
| | Retention time ≈20.8 min for Elafibranor |

Preparation of the Samples:

About 1 mg of the solid recrystallization residue was put in a 10 mL volumetric flask then dissolved to 10 ML with MeOH. Immediately after dissolution of the sample in MeOH, the solutions are processed, packaged and stored away from the light, Results:

All the crystallized samples (Form I to IV) correspond to elafibranor salts, with a purity percent of at least 99.7%.

X-Ray Powder Diffraction (XRPD) Analysis

X-ray powder diffraction (XRPD) analyses were performed on a Brüker AXS D2 Phaser, in a θ-θ configuration, using a copper anti-cathode, a mono-crystalline silicon sample holder and a Lynxeye detector. Instrument operating conditions for X-ray pattern acquisition are described in TABLE 2.

TABLE 2

| | | |
|---|---|---|
| | Temperature | Ambient |
| | Atmosphere | Ambient |
| X-rays generator | voltage (kV) | 30 |
| | intensity (mA) | 10 |
| X-rays source | target | Cu |
| | emission radiation Kλ1 (nm) | 0.15406 |
| | Kλ2 (nm) | 0.15444 |
| | ratio Kλ2/Kλ1 | 0.5 |
| | Kβ filter radiation | Nickel |
| Slit | anti-divergence (mm) | 0.6 |
| | anti-scattering (mm) | 8 |
| | Sollers slit (°) | 2.5 |
| Goniometer | angular sector analyzed (° for 2θ) | 0-70 |
| | step size (° for 2q) | 0.07 |
| | Rotation speed for sample holder (rpm) | 30 |
| Detection | step time for measuring diffracted intensity (s) | 1 |

Preparation of the Samples:

The powder sample is dispersed on the silicon sample holder in a way to avoid preferred orientation (not randomly oriented crystals) and to ensure planarity of the specimen surface. X-ray diffraction of Forms I, II and IV (anhydrous and dehydrate) are shown in FIGS. 20, 21, and 22 respectively.

Optical Microscopy (OM)

Characterization by optical microscopy is performed on a LEICA DMIRB microscope equipped with a digital camera and a motorized stage. Acquisition of microscopy patterns is performed with a Microvision Instruments image analysis station.

Preparation of the Samples:

A few milligrams of the tested sample are put onto a microscope glass plate with silicon oil, covered with a microscope glass slide, dispersed by a soft pressure applied onto the glass slide and then analyzed.

The various images are recorded with cross-polarized light.

Optical microscopy of Form I is shown in FIG. 1. Optical microscopy of Form II is shown in FIGS. 2a, 2b and 2c. Optical microscopy of Form III is shown in FIG. 3. Optical microscopy of Form IV is shown in FIGS. 4a, and 4b. Optical microscopy of Forms V, VI, VII, VIII, IX, X, XI, XII, XIII, XIV and XV are respectively shown in FIG. 5, FIG. 6. FIG. 7, FIG. 8, FIG. 9, FIG. 10, FIG. 11, FIG. 12, FIG. 13, FIG. 14 and FIG. 15.

Differential Scanning Calorimeter (DSC)

Differential scanning calorimeter (DSC) analysis is performed on a Q1000 TA Instruments analyzer. Sample is weighed in a non-airtight aluminum capsule, which is then crimped and put into the calorimeter oven. The samples were heated from room temperature to 200° C. A ramp rate of 5° C./minute was used and the oven was continuously on nitrogen purge flow at a 50 mL/min flow (Air Liquide gas, Alphagaz N2 quality)

The instrumental operating conditions for DSC profile acquisition are described in TABLE 3. DSC thermogram of Form I, II, III and IV are respectively shown in FIG. 16, FIG. 17, FIG. 18 and FIG. 19.

TABLE 3

| | | |
|---|---|---|
| Heater ramp (° C./min) | | 10 |
| Final temperature (° C.) | | 170° C. |
| Carrier gas | nitrogen | Messer, <<qualite Azote 5.0>> |
| flow rate (mL/min) | | 50 |

Photostability Protocol

Elafibranor salt powder was stressed by exposure to UV light according to ICH guidelines Q1B corresponding to 17 h of maximum exposition to UV light on a Heraeus SUNTEST CPS equipment.

For each elafibranor salt, a specimen of about 15 mg is placed in a quartz cell. In order to make the difference between the degradation only due to temperature within the SUNTEST apparatus chamber and the degradation only due to UV exposure, a second elafibranor salt sample protected from light is also placed in the SUNTEST chamber. All samples are then analyzed by HPLC.

In order to evidence any photostability improvement of each salt compared to the parent compound, the elafibranor free acid is also stressed by exposure to UV light following the same conditions as ones described for elafibranor salt samples.

Solubility Assessment

The solubility of the compound is determined in buffered aqueous solution at pH 1, pH 3, pH 5 and pH 7.4.

The saturation is obtained by adding an excess of active ingredient to a given volume of test medium. The suspension is stirred by orbital stirring over 24 hours at 20° C., away from light.

For elafibranor free acid and in all media, the soluble fraction is assessed after 24 hours. For elafibranor tromethamine salt and in all media the soluble fraction is assessed after 30 min, 1 hour, 2 hours and 24 hours in order to determine the maximum solubility levels accessible with the studied salt.

After 30 min, 1 hour, 2 hours and/or 24 hours, the supernatant is isolated by centrifugation and diluted in a solvent mixture allowing its injection into the chromatographic system. The concentration (expressed as parent concentration) in solution for each medium is determined by HPLC (external standardization).

After 24 hours an XRPD analysis is performed on the insoluble fraction isolated by centrifugation.

Preparation of Test Media:
- pH 1 HCl/KCl buffer: a mixture of 0.373 g of KCl and 13.4 ml of HCl in a 100 mL volumetric flask was completed to 100 mL with de-ionized water.
- pH 3 citrate buffer: 1.051 g of citric acid monohydrate was dissolved in 250 ml of de-ionized water. The pH was adjusted to 3 with NaOH.
- pH 5 citrate/phosphate buffer: Solution I was prepared: 2.8392 g of Na2HPO4 in 100 mL volumetric flask was completed to 100 mL with de-ionized water. Solution II was prepared: 2.1004 g of citric acid monohydrate in a 100 mL volumetric flask was completed to 100 mL with de-ionized water. To 48.5 mL of Solution II were added 51.5 mL of Solution I.
- pH 7.4 phosphate buffer: a mixture of 38 g of Na2HPO4, 12H2O and 3.8 g of Na2HPO4, 2H2O in a 1 L volumetric flask was completed to 1 L with de-ionized water.

Salt Screening

Macroscopic Observation

Several solid residues can be isolated for the associations of elafibranor with all counter-ions. For each of the tested counter-ions, the observed solid residues are not all presenting the same characteristics (color, size/quantity, shape of the solid residue and morphology of crystals if any visible). These characteristics are taken into account to select, for each counter-ion, relevant samples to be further characterized.

4 bases (benethamine, L-arginine, potassium hydroxide and sodium hydroxide), when associated to elafibranor, lead to the formation of noticeable solid residues in several crystallization media.

The association of the 11 others counter-ion bringing species to elafibranor leads to solid residues in some crystallization media but with lower quantity of solid material or only lead to liquid/vitreous residue with only a minor quantity of solid present in these vitreous residue.

Color of the Isolated Solids

It is important to note that surprisingly 5 of the 15 tested bases (benethamine, benzathine, L-arginine, potassium hydroxide and sodium hydroxide) when associated to elafibranor lead to white solids with a significant quantity of material in several crystallization media.

Optical Microscopy

A certain number of "counter-ion/crystallization medium" couples are selected for being observed by optical microscopy under cross-polarized light. The morphology of the crystals (when well defined crystal shapes are observed) can be compared between different samples. In the present case, optical microscopy analysis performed on different samples (solid residues) leads to identify well crystallized material in all observed samples.

Other Physical Characterizations

Further spectrometric and melting temperature range comparisons have been performed on each potential salt hit of interest to finalize a ranking between all tested counter-ions.

For hot-stage microscopy experiments, the thermal behaviors of the analyzed samples are summarized in TABLE 4 (samples of elafibranor crystallized alone from various media are also analyzed for comparison purpose).

Synthesis

Synthesis of elafibranor ("the compound" in the following experimental part) was realized according to the method described in WO2011144579, then crude material was recrystallized in isopropanol.

TABLE 4 presents the list of tested bases (counter-ions) and the corresponding reactant and their supplier.

TABLE 4

| Counter-ions | Reactant | Supplier | Reference |
|---|---|---|---|
| Tromethamine | Tromethamine | Sigma | T6687-100G |
| Benethamine | Benethamine | Aldrich | 261742-5G |
| Ethanolamine | Ethanolamine | Sigma-Aldrich | 398136 |
| Meglumine | Meglumine | Sigma | M9179-100G |
| Glycine | Glycine | Sigma | G7126-100G |
| Benzathine | Benzathine | Aldrich | D35201-25G |
| Erbumine | ter-Butylamine | Aldrich | B8,920-5 |
| L-Lysine | L-Lysine | Sigma | L5501-5G |
| L-Arginine | L-Arginine | Sigma | A8094-25G |
| Choline | Choline OH | Aldrich | 26972-250ML |
| Potassium | Potassium hydroxide (86.2%) | Sigma-Aldrich | 30603-500G |
| Sodium | Sodium hydroxide | Carlo-Erba | 480717000 |
| Epolamine | Hydroxyethyl-pyrrolidine | Aldrich | H29404-5ML |
| Magnesium | Magnesium hydroxide | Fluka | 63081 |
| 2-amino-2-methyl-propan-1-ol | 2-amino-2-methyl-propan-1-ol | Fluka | 08578-50ML |

Example 1: Tromethamine Salt (Form I)

To 1020.13 mg of elafibranor free acid is added a quantity of 321.45 mg of tromethamine corresponding to a 1:1 stoichiometry. 4.05 mL of ethanol are added and the suspension is stirred, away from light, at 70° ° C. until complete solubilization within 20 minutes. 54 mL of ethyl acetate are then added. The solution is stirred at 70° C. and the crystallization occurred within 60 minutes (always away from light): appearance of aggregated white particles that are birefringent when observed in cross-polarized light.

The suspension of the tromethamine salt is allowed to cool down at room temperature (away from light) and the supernatant is removed by filtration. During the filtration, the solid material is washed once by several milliliters of the first filtrate (brought back into the crystallization balloon for removing solid residues) and then once with several milliliters of ethyl acetate. The powder is finally dried under vacuum at 90° C. for 2 hours.

The resulting yield is about 92% (about 1.3 g recovered).

Microscopy observations of the isolated sample are reported on FIG. 1. The high birefringence of particles when observed between crossed polarizer and analyzer indicates the sample is well crystallized.

The crystallized sample thermogram displays only one strong endothermic event, detected at an onset temperature of 149° C. that corresponds to the melting point of elafibranor tromethamine salt.

The HPLC profile (FIG. 24) shows no degradation of the active ingredient in the isolated solid compared to the reference parent compound. The batch purity is 99.96%.

FIG. 20 shows X-ray diffraction profile of Salt I (crystallized in EtOH/AcEt) and TABLE 5 lists the numerical values of the XRPD peak position of FIG. 20 diffractogram.

TABLE 5

| Angle | Inter-reticular | Intensity | |
|---|---|---|---|
| 2-θ (°) | distance (Å) | c.p.s. | % |
| 6.5 | 13.7 | 6957 | 100 |
| 12.2 | 7.2 | 2874 | 41.3 |

TABLE 5-continued

| Angle 2-θ (°) | Inter-reticular distance (Å) | Intensity c.p.s. | Intensity % |
|---|---|---|---|
| 12.9 | 6.9 | 2016 | 29.0 |
| 13.5 | 6.5 | 1229 | 17.7 |
| 14.1 | 6.3 | 2567 | 36.9 |
| 14.7 | 6.0 | 2357 | 33.9 |
| 15.0 | 5.9 | 6632 | 95.3 |
| 15.3 | 5.8 | 4278 | 61.5 |
| 15.6 | 5.7 | 2637 | 37.9 |
| 16.1 | 5.5 | 2454 | 35.3 |
| 16.9 | 5.2 | 3787 | 54.4 |
| 17.3 | 5.1 | 3758 | 54.0 |
| 17.6 | 5.0 | 4543 | 65.3 |
| 18.4 | 4.8 | 4248 | 61.1 |
| 19.0 | 4.7 | 2417 | 34.7 |
| 19.4 | 4.6 | 4222 | 60.7 |
| 20.1 | 4.4 | 1281 | 18.4 |
| 20.6 | 4.3 | 2331 | 33.5 |
| 22.2 | 4.0 | 2041 | 29.3 |
| 22.6 | 3.9 | 6503 | 93.5 |
| 23.4 | 3.8 | 1611 | 23.2 |
| 24.0 | 3.7 | 784 | 11.3 |
| 24.6 | 3.6 | 1597 | 23.0 |
| 24.9 | 3.6 | 2230 | 32.1 |
| 25.3 | 3.5 | 1531 | 22.0 |
| 25.9 | 3.4 | 1877 | 27.0 |
| 26.4 | 3.4 | 737 | 10.6 |
| 27.1 | 3.3 | 734 | 10.6 |
| 28.2 | 3.2 | 669 | 9.6 |
| 28.5 | 3.1 | 883 | 12.7 |
| 29.2 | 3.1 | 1281 | 18.4 |
| 29.7 | 3.0 | 764 | 11.0 |
| 31.5 | 2.8 | 1166 | 16.8 |
| 31.8 | 2.8 | 880 | 12.7 |
| 32.5 | 2.8 | 1339 | 19.2 |
| 33.2 | 2.7 | 595 | 8.6 |
| 34.3 | 2.6 | 521 | 7.5 |
| 35.5 | 2.5 | 572 | 8.2 |
| 36.6 | 2.5 | 613 | 8.8 |
| 37.1 | 2.4 | 658 | 9.5 |
| 38.1 | 2.4 | 550 | 7.9 |
| 38.8 | 2.3 | 490 | 7.0 |
| 39.3 | 2.3 | 599 | 8.6 |
| 42.7 | 2.1 | 797 | 11.5 |
| 44.4 | 2.0 | 685 | 9.8 |
| 46.1 | 2.0 | 640 | 9.2 |

Based on the XRPD and HPLC results, we can conclude that the stoichiometry elafibranor:tromethamine is 1:1.

Different solubility test at different pH were performed. It appears that elafibranor tromethamine salt is more soluble than elafibranor at pH 7.4 (see TABLE 6).

TABLE 6

| Media | Soluble fraction (mg/mL) at 20° C. at 24 hours Form I | Soluble fraction (mg/mL) at 20° C. at 24 hours Elafibranor free acid | Final pH of the saturated solution Form I | Final pH of the saturated solution Elafibranor free acid |
|---|---|---|---|---|
| pH 1 HCl/KCl buffer | <0.001 | <0.001 | 0.9 | 0.7 |
| pH 3 citrate buffer | <0.001 | <0.001 | 3.1 | 2.9 |
| pH 5 citrate/phosphate buffer | 0.003 | 0.001 | 5.1 | 4.9 |
| pH 7.4 phosphate buffer | 0.19 | 0.13 | 7.3 | 7.3 |

Example 2: Potassium Salt (Form II)

Sample Crystallized in CH3CN

A quantity of 42.29 mg of potassium hydroxide is added to about 243 mg of elafibranor free acid, corresponding to a 1:1 stoichiometry. For solubilization, 4 mL of ethanol are added (stirring on a rotary evaporator at 70° C.). The stirring is extended a few minutes for a completed dissolution. Solvent (ethanol) is then evaporated to dryness at 70° C. leading to a film. The film is re-suspended with 4 mL of acetonitrile which leads to immediate crystallization. The resulting suspension is then kept at sub-ambient temperature for 2 hours to allow a more important crystallization. The supernatant is removed from the flask and the sample is washed twice with acetonitrile before the powder is finally dried under dynamic vacuum for about 1 hour at 90° C.

The resulting yield is about 75%.

The percentage of elafibranor in this salt sample, determined by external standardization, is found to be 89.6% by HPLC which is not significantly different from the 91.0% theoretical Elafibranor fraction in the targeted elafibranor potassium salt (FIG. 25).

Microscopy observations of the produced sample are reported on FIG. 2c. The birefringence of particles when observed between crossed polarizer and analyzer indicates the sample is crystallized.

The crystallized sample thermogram displays two major events (see FIG. 15):

- A broad and small endothermic transition, detected with an onset temperature of 185° C., could correspond whether to a glass transition associated to an enthalpic relaxation or a solid-solid transition;
- A strong endothermic event detected with an onset temperature of 247° C.; this second event most probably corresponds to the melting of the elafibranor potassium salt.

FIG. 21 shows X-ray diffraction profile of Salt II (crystallized in CH3CN) and TABLE 7 lists the numerical values of the XRPD peak position of FIG. 21 diffractogram.

TABLE 7

| Angle 2-θ (°) | Inter-reticular distance (Å) | Intensity c.p.s. | Intensity % |
|---|---|---|---|
| 4.6 | 19.2 | 156 | 13.1 |
| 5.8 | 15.3 | 62 | 5.2 |
| 6.5 | 13.5 | 151 | 12.7 |
| 8.0 | 11.4 | 1188 | 100.0 |
| 11.7 | 7.6 | 181 | 15.2 |
| 12.1 | 7.3 | 75 | 6.3 |
| 13.1 | 6.7 | 127 | 10.7 |
| 13.6 | 6.5 | 156 | 13.1 |
| 17.7 | 5.0 | 118 | 9.9 |
| 18.1 | 4.9 | 97 | 8.2 |
| 25.6 | 3.5 | 115 | 9.7 |
| 26.9 | 3.3 | 106 | 8.9 |
| 27.4 | 3.3 | 105 | 8.8 |

Based on the XRPD and HPLC results, we can conclude that the stoichiometry elafibranor:potassium is 1:1.

Example 3: Sodium Salt (Form III)

Sample Crystallized in Acetone

About 103 mg of elafibranor free acid are first solubilized in 1 mL of acetone (stirring on a rotary evaporator at) 50° ° C. A volume of 268 μL sodium hydroxide 1N corresponding to a 1:1 stoichiometry is then added, and the stirring is maintained for a few minutes. The resulting solution is allowed to cool down to room temperature and then kept at sub-ambient temperature. After a storage period of 4 days, a massive crystallization is observed.

The supernatant is removed from the flask and the powder is finally dried under dynamic vacuum for about 2 hours at 90° C. The resulting yield is about 93%.

The percentage of elafibranor in this salt sample is found to be 87.3% by HPLC. The HPLC profiles show no degradation of the active ingredient in the isolated solid compared to the reference parent compound (FIG. 26).

Microscopy observations of the produced sample are reported on FIG. 3. The high birefringence of particles when observed between crossed polarizer and analyzer indicates the sample is well crystallized.

The crystallized sample thermogram displays three major events (see FIG. 16):
- A broad endothermic transition, detected with an onset temperature of 22° C., corresponding either to the end of drying or to the loss of adsorbed water on the bulk;
- A small exothermic event, detected with an onset temperature of 209° C., that could correspond either to the crystallization of an amorphous fraction of the salt into the crystallized salt form, or to a solid-solid transition;
- A strong endothermic event detected with an onset temperature of 261° C.; this third event corresponds to the melting of the elafibranor sodium salt Based on the DSC and HPLC results, we can conclude that the stoichiometry elafibranor:sodium is 1:1.

Example 4a: Arginate Salt (Form IV)

General procedure: to about 214 mg of elafibranor free acid is added a quantity of 97.10 mg of L-arginine corresponding to a 1:1 stoichiometry. For solubilization, 6 mL of acetone and 1.5 mL of water are added (stirring on a rotary evaporator at 50° C.). Before the complete solubilization of both compounds, a recrystallization occurs with appearance of white and flake-like solid residue.

Sample Crystallized in Acetone
  The resulting suspension is allowed to cool down to room temperature and is then washed with acetone and dioxane 1-4, and dried under vacuum before the particules are finally re-suspended in cateone. The washed residue in suspension in acetone is kept at sub-ambient temperature. After a storage period of 14 days, a suspension with very small particules is observed.
  The powder is finally isolated by filtration under vacuum.
  The resulting yield is about 84%.
  Microscopy pictures of the produced sample are reported on FIG. 4a. The birefringence of particles when observed between crossed polarizer and analyzer indicates the sample is crystallized.
  The crystallized sample thermogram displays 3 endothermic events which show that the batch contains native elafibranor free acid.

Sample Crystallized in Acetone/H2O
  The stirring is extended to 30 minutes for a more important crystallization to occur. The powder is finally isolated by filtration under vacuum.
  The resulting yield is about 82%.
  The percentage of elafibranor in this salt sample is found to be 68% by HPLC which is not significantly different from the 71.1% theorical elafibranor fraction in the targeted elafibranor arginate salt. The HPLC profiles show no degradation of the active ingredient in the isolated solid compared to the reference parent compound (FIG. 26).
  Microscopy observations of the produced sample are reported on FIG. 4b. The birefringence of particles when observed between crossed polarizer and analyzer indicates the sample is crystallized.
  The crystallized sample thermogram displays only one strong endothermic event, detected at an onset temperature of 167° C., that corresponds to the melting, concomitant with thermal decomposition (erratic signal), of the elafibranor arginate salt.

FIG. 22 shows X-ray diffraction profile of Salt IV (crystallized in acetone/$H_2O$) and TABLE 8 lists the numerical values of the XRPD peak position of FIG. 22 diffractogram.

TABLE 8

| Angle | Inter-reticular | Intensity | |
|---|---|---|---|
| 2-θ (°) | distance (Å) | c.p.s. | % |
| 3.0 | 29.4 | 894 | 83.3 |
| 5.9 | 14.9 | 1073 | 100.0 |
| 8.1 | 10.9 | 66 | 6.2 |
| 8.8 | 10.1 | 124 | 11.6 |
| 9.5 | 9.3 | 62 | 5.8 |
| 11.7 | 7.5 | 107 | 10.0 |
| 12.8 | 6.9 | 94 | 8.8 |
| 13.2 | 6.7 | 118 | 11.0 |
| 13.9 | 6.4 | 74 | 6.9 |
| 14.7 | 6.0 | 98 | 9.1 |
| 15.1 | 5.9 | 90 | 8.4 |
| 15.6 | 5.7 | 85 | 7.9 |
| 16.7 | 5.3 | 100 | 9.3 |
| 17.4 | 5.1 | 39 | 3.6 |
| 17.6 | 5.0 | 87 | 8.1 |
| 18.2 | 4.9 | 75 | 7.0 |
| 18.7 | 4.7 | 57 | 5.3 |
| 19.1 | 4.6 | 90 | 8.4 |
| 19.3 | 4.6 | 46 | 4.3 |
| 19.8 | 4.5 | 114 | 10.6 |
| 19.9 | 4.5 | 112 | 10.4 |
| 21.0 | 4.2 | 95 | 8.9 |
| 21.6 | 4.1 | 37 | 3.4 |
| 22.1 | 4.0 | 74 | 6.9 |
| 23.2 | 3.8 | 86 | 8.0 |
| 24.4 | 3.6 | 71 | 6.6 |
| 25.2 | 3.5 | 45 | 4.2 |
| 26.0 | 3.4 | 49 | 4.6 |
| 26.7 | 3.3 | 46 | 4.3 |
| 27.1 | 3.3 | 39 | 3.6 |
| 27.7 | 3.2 | 51 | 4.8 |
| 28.3 | 3.1 | 44 | 4.1 |
| 29.7 | 3.0 | 40 | 3.7 |
| 30.2 | 3.0 | 35 | 3.3 |
| 30.7 | 2.9 | 32 | 3.0 |
| 32.6 | 2.7 | 45 | 4.2 |
| 33.3 | 2.7 | 31 | 2.9 |
| 34.6 | 2.6 | 42 | 3.9 |
| 35.6 | 2.5 | 51 | 4.8 |
| 38.0 | 2.4 | 25 | 2.3 |
| 38.4 | 2.3 | 20 | 1.9 |
| 40.0 | 2.3 | 24 | 2.2 |
| 42.0 | 2.1 | 29 | 2.7 |
| 44.1 | 2.1 | 27 | 2.5 |
| 51.2 | 1.8 | 21 | 2.0 |
| 65.0 | 1.4 | 16 | 1.5 |

Based on the DSC and HPLC results, we can conclude that the stoichiometry elafibranor:arginate is 1:1.

Example 4b: Arginate Hydrate Salt

A sample of about 20 mg of EXAMPLE 4a is submitted to a Dynamic Vapor Sorption (DVS) cycle with a stop at 60% RH in desorption phase. The relative humidity is then maintained at 60% so that the generated hydrate form can be characterized.

The comparison of the water sorption experiment to obtain the hydrated analytical sample to the first DVS cycle performed on the anhydrous salt form batch (EXAMPLE 4a) confirms that the same conversion has occurred.

The analyzed powder of the hydrated elafibranor L-arginate salt exhibits several diffraction peaks showing the studied material is crystalline.

FIG. 23 shows X-ray diffraction profile of Salt IV dihydrate (crystallized in acetone/$H_2O$) and TABLE 9 lists the numerical values of the XRPD peak position of FIG. 23 diffractogram.

TABLE 9

| Angle | Inter-reticular | Intensity | |
|---|---|---|---|
| 2-θ (°) | distance (Å) | c.p.s. | % |
| 2.8 | 31.6 | 1362 | 100.0 |
| 5.5 | 16.2 | 492 | 36.1 |
| 7.0 | 12.7 | 33.7 | 2.5 |
| 8.1 | 10.8 | 130 | 9.5 |
| 8.7 | 10.2 | 70 | 5.1 |
| 10.8 | 8.2 | 87 | 6.4 |
| 12.2 | 7.3 | 65 | 4.8 |
| 13.6 | 6.5 | 54 | 4.0 |
| 14.4 | 6.2 | 69 | 5.1 |
| 15.3 | 5.8 | 45 | 3.3 |
| 16.2 | 5.5 | 59 | 4.3 |
| 16.4 | 5.4 | 59 | 4.3 |
| 17.3 | 5.1 | 87 | 6.4 |
| 17.8 | 5.0 | 38 | 2.8 |
| 18.2 | 4.9 | 43 | 3.2 |
| 19.2 | 4.6 | 56 | 4.1 |
| 20.2 | 4.4 | 52 | 3.8 |
| 21.1 | 4.2 | 65 | 4.8 |
| 22.5 | 4.0 | 43 | 3.2 |
| 24.4 | 3.6 | 58 | 4.3 |

Example 5: Benethamine Salt (Form V)

Elafibranor free acid (1 eq) was crystallized with 1 molar equivalent of benethamine in Acetone/$H_2O$.

Microscopy observations of the produced sample are reported on FIG. 5. The birefringence of particles when observed between crossed polarizer and analyzer indicates the sample is crystallized.

Example 6: Benzathine Salt (Form VI)

Elafibranor free acid (1 eq) was crystallized with 1 molar equivalent of benzathine in Acetone/H2O.

Microscopy observations of the produced sample are reported on FIG. 6. The birefringence of particles when observed between crossed polarizer and analyzer indicates the sample is crystallized.

Example 7: Ethanolamine Salt (Form VII)

Elafibranor free acid (1 eq) was crystallized with 1 molar equivalent of ethanolamine in Acetone/H2O.

Microscopy observations of the produced sample are reported on FIG. 7. The birefringence of particles when observed between crossed polarizer and analyzer indicates the sample is crystallized.

Example 8: Meglumine Salt (Form VIII)

Elafibranor free acid (1 eq) was crystallized with 1 molar equivalent of meglumine in Acetone.

Microscopy observations of the produced sample are reported on FIG. 8. The birefringence of particles when observed between crossed polarizer and analyzer indicates the sample is crystallized.

Example 9: Glycine Salt (Form IX)

Elafibranor free acid (1 eq) was crystallized with 1 molar equivalent of glycine in Acetone/H2O.

Microscopy observations of the produced sample are reported on FIG. 9. The birefringence of particles when observed between crossed polarizer and analyzer indicates the sample is crystallized.

Example 10: Erbumine Salt (Form X)

Elafibranor free acid (1 eq) was crystallized with 1 molar equivalent of t-butylamine in Acetone/H2O.

Microscopy observations of the produced sample are reported on FIG. 10. The birefringence of particles when observed between crossed polarizer and analyzer indicates the sample is crystallized.

Example 11: L-Lysine Salt (Form XI)

Elafibranor free acid (1 eq) was crystallized with 1 molar equivalent of L-lysine in EtOH/H2O.

Microscopy observations of the produced sample are reported on FIG. 11. The birefringence of particles when observed between crossed polarizer and analyzer indicates the sample is crystallized.

Example 12: Choline Salt (Form XII)

Elafibranor free acid (1 eq) was crystallized with 1 molar equivalent of choline-OH in Acetone/H2O.

Microscopy observations of the produced sample are reported on FIG. 12. The birefringence of particles when observed between crossed polarizer and analyzer indicates the sample is crystallized.

Example 13: Epolamine Salt (Form XIII)

Elafibranor free acid (1 eq) was crystallized with 1 molar equivalent of hydroxyethyl-pyrrolidine in THF/H2O.

Microscopy observations of the produced sample are reported on FIG. 13. The birefringence of particles when observed between crossed polarizer and analyzer indicates the sample is crystallized.

Example 14: Magnesium Salt (Form XIV)

Elafibranor free acid (1 eq) was crystallized with 1 molar equivalent of magnesium hydroxide in H2O.

Microscopy observations of the produced sample are reported on FIG. 14. The birefringence of particles when observed between crossed polarizer and analyzer indicates the sample is crystallized.

Example 15: 2-amino-2-methyl-propan-1-ol salt (Form XV)

Elafibranor free acid (1 eq) was crystallized with 1 molar equivalent of 2-amino-2-methyl-propan-1-ol in H2O.

Microscopy observations of the produced sample are reported on FIG. 15. The birefringence of particles when observed between crossed polarizer and analyzer indicates the sample is crystallized.

Example 16: Photostability

The crystallized samples were stressed by exposure to UV light according to the photostatbility protocol described above.

Different photostability tests were performed. The following TABLE 10 displays the results obtained for elafibranor free acid and elafibranor salts.

| Storage condition | % of unchanged elafibranor determined by HPLC after UV exposure (HPLC-UV at 350 nm) | | | |
|---|---|---|---|---|
| | Free acid (expected elafibranor 100%) | Trométhamine salt (Form I) | Potassium salt (Form II) | Arginate salt (Form IV) |
| Elafibranor degradation (%) | 27 | 10 | 13 | 4 |

With only 4% degradation after 17 h exposure to UV light in the test conditions, elafibranor L-arginate salt (Form IV; example 4a) is found to be the most stable tested bulk compared to elafibranor free acid (27% degradation), elafibranor sodium salt (Form III; 89% degradation), elafibranor potassium salt (Form II; 13% degradation) and elafibranor tromethamine salt (Form I; 10% degradation).

The tested elafibranor L-arginate salt (Form IV), elafibranor potassium salt (Form II) and elafibranor tromethamine salt (Form I) present a significant improvement of the photostability compared the elafibranor free acid.

Example 17: In Vitro Test

Materials & Methods

Compounds were dissolved in dimethyl sulfoxide (DMSO, Sigma Aldrich cat #276855). SB525334 (Sigma Aldrich cat #S8822), Crenolanib (Selleckchem cat #S2730), TGFβ1 (PeproTech cat #100-21), PDGF-BB (Peprotech cat #100-14B) and Rosiglitazone (Yick-Vic Chemicals & Pharmaceuticals cat #PH-4472B) were obtained commercially. Fenofibric acid and GW501516 were synthesized by Genfit.

Gal4-PPAR Assays

Monkey kidney COS-7 cells were maintained in standard culture conditions (Dulbecco's modified Eagle's minimal medium: DMEM) supplemented with 10% fetal calf serum, 1% sodium pyruvate, 1% essential amino acids, 1% L-glutamine and 1% antibiotics at 37° C. in a humidified atmosphere of 5% $CO_2$ and 95% air. The medium was changed every 2 days. All tested compounds were dissolved in DMSO. Cells were transfected using 4 µl JetPEI™ (Polyplus transfection)/µg of DNA. Briefly, 150 ng of DNA per well was transfected in a 96 well culture plate of adherent COS-7 cells (respecting the 10:1 ratio between the Gal4(RE)_TkpGL3 plasmid and the plasmid coding the nuclear receptor of interest (pGal4-hPPARalpha, pGal4-hPPARgamma, pGal4-hPPARdelta, pGal4-mPPARalpha, pGal4-mPPARgamma and pGal4-mPPARdelta) or of the pGal4phi plasmid (negative control). Cells were enzymatically detached and seeded in 96 well plates at the density of 40,000 cells per well and then incubated for 24 hours at 37° C. The activation was performed in DMEM 0% fetal calf serum, supplemented with the tested compounds (compound of interest or reference molecules) or vehicle (DMSO 0.1%). The luciferase activity was measured with the Steady-Glo Luciferase Assay System (Promega, Madison, WI). All transactivation experiments were performed at least 2 times. Activation curves were realized using Prism® (from GraphPad) software. Prism® was also used to fit the standard curves and then determine the specific $EC_{50}$ values, maximum effect versus reference molecules and Hill slope. The Emax effect of each new ligand is represented as the ratio of the maximal induction (plateau) obtained with the new ligand and the induction obtained with the corresponding reference compound. The reference compounds for PPARalpha, PPARgamma and PPARdelta were fenofibrate (100 µM), rosiglitazone (10 µM) and GW501516 (1 µM), respectively.

hHSC Culture

The human primary hepatic stellate cells (hHSC) (ScienCell, Innoprot) were cultured in STeCM medium (ScienCell cat #5301) that was supplemented with 2% fetal bovine serum (FBS, ScienCell cat #0010), 1% penicillin/streptomycin (ScienCell cat #0503) and stellate cell growth supplement (SteCGS; ScienCell cat #5352). Cell culture flasks were coated with Poly-L Lysine (Sigma cat #P4707) for a better adherence.

Determination of PDGF-Induced Proliferation of hHSC

The hHSC were cultured under standard conditions, as described above. The cells were subsequently plated at a density of $1.2 \times 10^4$ cells per well into 96-well plates and were cultured overnight at 37° C. and 5% $CO_2$, followed by washing of cells with Phosphate Buffer Saline (PBS, Invitrogen cat #14190) and replacing the growth medium with a serum-free and SteCGS-free medium for an additional 24 hours. Cells were pre-treated with all compounds for 1 hour before the addition of PDGF-BB (10 ng/ml). Treatments were then continued for an additional 20 hours. Cell proliferation was measured by bromodeoxyuridine (BrdU) incorporation using a BrdU labeling and detection kit (Roche cat #11647229001). BrdU labeling solution was added to cells, followed by incubation for another 4 hours before fixation, addition of nucleases, addition of anti-BrdU-POD and peroxidase substrate. The absorbance at 405 nm (with a reference wavelength at 690 nm) was measured using an ELISA plate reader (Tecan).

TGF-β1-Induced Activation of hHSC

The hHSC were cultured under standard conditions, as described above. The cells were subsequently plated at a density of $7 \times 10^4$ cells per well into 24-well plates for gene expression studies, and at a density of $2 \times 10^4$ cells per well into 96-well plates for the measure of α-SMA by ELISA. The next day, cell-culture medium was removed, and cells were washed with PBS (Invitrogen cat #14190). hHSC were deprived for 24 hours in serum-free and SteCGS-free medium. For the treatments with compounds according to the invention the serum-deprived hHSC were preincubated for 1 hour with the compounds followed by addition of the profibrogenic stimuli TGFβ1 (1 ng/mL) in serum-free and SteCGS-free medium for an additional 24 hour period.

α-SMA ELISA

The level of α-SMA was measured using a Sandwich ELISA. Briefly, the wells of an ELISA plate were first coated with the capture antibody (mouse monoclonal anti-ACTA2, Abnova) at 4° C. overnight. After 3 washes in PBS +0.2% Tween 20, a blocking solution consisting of PBS +0.2% BSA was added for one hour followed by another washing cycle. The cell lysates were transferred into the wells for binding to the capture antibody for a period of 2 h at room temperature. After the washing procedure, the detection antibody (biotinylated mouse monoclonal anti-ACTA2, Abnova) was added for 2 hours at room temperature followed by 3 washes. For the detection, an HRP-conjugated Streptavidin (R&D Systems cat #DY998) was first applied for 30 min at room temperature. After washing, the HRP substrate TMB (BD Bioscience, cat #555214) was added and incubated for 7 min at room temperature in the dark. Upon oxidation, TMB forms a water-soluble blue reaction product that becomes yellow with addition of sulfuric acid (solution stop), enabling accurate measurement of the intensity at 450 nm using a spectrophotometer. The developed color is directly proportional to the amount of α-SMA present in the lysate.

Gene Expression

Total RNA was isolated using RNeasy Mini Kit (Qiagen) following manufacturer's instructions. Total RNA (200 ng for in vitro samples) were reverse transcribed into cDNA using M-MLV RT (Moloney Murine Leukemia Virus Reverse Transcriptase) (Invitrogen cat #28025) in 1×RT buffer (Invitrogen), 0.5 mM DTT (Invitrogen), 0.18 mM dNTPs (Promega), 200 ng pdN6 (Amersham) and 30U of RNase inhibitor (Promega).

Quantitative PCR was then carried out using the CFX96 Touch™ Real-Time PCR Detection System (Biorad). Briefly, the PCR reactions were performed in 96-WP format in 25 µl of total volume containing 1 µL of reverse transcription reaction, 0.5 µL of reverse and forward primers (10 pmol each), and 12.5 µl of 2× iQ SYBR Green Supermix (BioRad).

TABLE 11

Human Primers

| Primer name | Sequence (5'->3') |
| --- | --- |
| 36B4 forward | CATGCTCAACATCTCCCCCTTCTCC (SEQ ID NO: 1) |
| 36B4 reverse | GGGAAGGTGTAATCCGTCTCCACAG (SEQ ID NO: 2) |
| COL1A1 forward | AATGGTGCTCCTGGTATTGC (SEQ ID NO: 3) |
| COL1A1 reverse | ACCAGGTTCACCGCTGTTAC (SEQ ID NO: 4) |
| ACTA2 forward | CATGCTCAACATCTCCCCCTTCTCC (SEQ ID NO: 5) |
| ACTA2 reverse | CATGCTCAACATCTCCCCCTTCTCC (SEQ ID NO: 6) |
| COL4A1 forward | GTTGGTCTACCGGGACTCAA (SEQ ID NO: 7) |
| COL4A1 reverse | GTTCACCTCTGATCCCCTGA (SEQ ID NO: 8) |

Expression levels were normalized using the expression of 36B4 gene as a reference in human samples.

For each gene, the standard curves were drawn by selecting the best points (at least three points) in order to have PCR reaction efficiency close to 100% and a correlation coefficient close to 1. Expression levels were determined using the standard curve equation for both the housekeeping gene and the target gene (taking into account the specific PCR efficiency of each target gene).

Results and Conclusions:

TABLE 12 and 13 show that compounds according to the invention have activities on the three PPAR isoforms (human and murine, respectively) similar to the free acid elafibranor.

TABLE 12

| | Human | | |
| --- | --- | --- | --- |
| | PPARalpha EC50 (µM) | PPARgamma EC50 (µM) | PPARdelta EC50 (µM) |
| Elafibranor | 0.057 | 0.43 | 0.42 |
| Elafibranor Sodium salt | 0.077 | 0.56 | 0.56 |
| Elafibranor L-Arginine salt | 0.054 | 0.32 | 0.38 |
| Elafibranor Potassium salt | 0.064 | 0.43 | 0.47 |
| Elafibranor Tromethamine salt | 0.068 | 0.49 | 0.51 |

TABLE 13

| | Murin | | |
| --- | --- | --- | --- |
| | PPARalpha EC50 (µM) | PPARgamma EC50 (µM) | PPARdelta EC50 (µM) |
| Elafibranor | 0.095 | 0.58 | 1.03 |
| Elafibranor Sodium salt | 0.133 | 0.77 | 1.75 |
| Elafibranor L-Arginine salt | 0.093 | 0.58 | 0.95 |
| Elafibranor Potassium salt | 0.096 | 0.59 | 1.33 |
| Elafibranor Tromethamine salt | 0.103 | 0.73 | 1.80 |

Excessive activity of PDGF has been associated with several human disorders, including organ fibrosis and tumorigenesis. PDGF plays a key role in expansion of myofibroblasts by stimulating their proliferation, migration and survival. Unexpectedly, our experimental data showed that the compounds according to the invention inhibit, in a dose-dependent way, the proliferation of hHSC that was induced by a treatment with PDGF-BB (FIG. 28). As demonstrated on FIGS. 28, the efficacy of the compounds according to the invention is comparable to that of a selective PDGFR inhibitor, Crenolanib.

The abnormal persistence of differentiated myofibroblasts is a characteristic of many fibrotic diseases. Following liver injury, quiescent HSC undergo a process of activation that is characterized by a differentiation into (α-SMA)-positive myofibroblasts. Compounds according to the invention reduced either α-SMA protein secretion (FIG. 29) or gene expression in TGFβ1-activated hHSC. Other markers of TGFβ1 stimulation were reduced by compounds according to the invention including the extracellular matrix collagen 1A1 (COL1A1) (FIG. 30) and matrix collagen 4A1 (COL4A1) (FIG. 31). Toxicity assays confirmed that the reduced levels of α-SMA were not due to toxicity or apoptosis of hHSC.

In conclusion, the applicant has shown antifibrotic activities for compounds according to the invention. These results demonstrate that compounds according to the invention can provide therapeutic benefits in multiple types of fibrotic diseases.

The invention claimed is:

1. A crystalline salt of elafibranor, selected from the group consisting of a tromethamine salt (salt I), a potassium salt (salt II), and an L-arginine salt (salt IV), of elafibranor.

2. The crystalline salt according to claim 1, which is the tromethamine salt of elafibranor having an X-ray powder diffraction pattern comprising peaks (2θ in angular degrees ±0.2°) at 6.5°, 12.2°, 15.0°, 15.3°, 16.9°, 17.3°, 17.6°, 18.4°, 19.4°, and 22.6°.

3. The crystalline salt according to claim 1, which is the potassium salt of elafibranor having an X-ray powder diffraction pattern comprising peaks (2θ in angular degrees ±0.2°) at 4.6°, 8.0°, 11.7°, 13.1°, and 13.6°.

4. The crystalline salt according to claim 1, which is the L-arginine salt of elafibranor having an X-ray powder diffraction pattern comprising peaks (2θ in angular degrees ±0.2°) at 5.9°, 8.8°, 11.7°, 13.2°, 19.8°, and 19.9°.

5. A method for preparing a crystalline salt of elafibranor comprising the steps of:

(i) away from the light, dissolving the free acid of Formula (I) and a base providing the counter-ion for salt formation at an acid/base molar ratio which is selected from 1:1 to 2:1 depending on the base in a suitable solvent

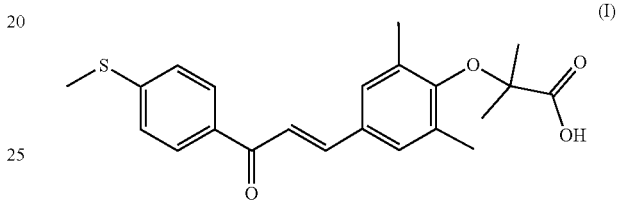

(ii) stirring the free acid of Formula (I) and the base at a temperature from 40° C. to 100° ° C., (iii) adding a suitable solvent to mixture obtained in (ii) and slowly cooling down to room temperature or (iii) removing the solvent of mixture obtained in (ii), adding a suitable crystallization solvent to the residue, and (iv) isolating the precipitated crystals by filtration.

6. A pharmaceutical composition comprising the crystalline salt of elafibranor according to claim 1, and a pharmaceutically acceptable carrier.

7. The pharmaceutical composition according to claim 6, which is formulated in the form of injectable suspensions, gels, oils, pills, suppositories, powders, gel caps, capsules, aerosols or means of galenic forms or devices assuring a prolonged and/or slow release.

8. A method of treating a disease selected in the group consisting of non-alcoholic fatty liver disease (NAFLD), non-alcoholic steatohepatitis (NASH), liver fibrosis and liver cirrhosis, comprising administering to a subject in need thereof a therapeutically effective amount of the crystalline salt of claim 1.

* * * * *